(12) United States Patent
Ghosh et al.

(10) Patent No.: US 11,911,413 B2
(45) Date of Patent: Feb. 27, 2024

(54) METHODS AND COMPOSITIONS FOR THE TREATMENT OF PAIN AND/OR INFLAMMATION

(71) Applicants: Proteobioactives Pty Limited, Fairlight (AU); Nancy Wilson-Ghosh, Fairlight (AU)

(72) Inventors: Peter Ghosh, Fairlight (AU); Jack Edelman, Subiaco (AU)

(73) Assignee: Proteobioactives Pty Limited, Fairlight (AU)

( * ) Notice: Subject to any disclaimer, the term of this patent is extended or adjusted under 35 U.S.C. 154(b) by 0 days.

(21) Appl. No.: 16/970,049

(22) PCT Filed: Feb. 15, 2019

(86) PCT No.: PCT/AU2019/050119
§ 371 (c)(1),
(2) Date: Aug. 14, 2020

(87) PCT Pub. No.: WO2019/157560
PCT Pub. Date: Aug. 22, 2019

(65) Prior Publication Data
US 2021/0093658 A1 Apr. 1, 2021

(30) Foreign Application Priority Data
Feb. 16, 2018 (AU) ................................ 2018900504

(51) Int. Cl.
| | | |
|---|---|---|
| A61K 31/737 | (2006.01) | |
| A61K 9/00 | (2006.01) | |
| A61K 9/48 | (2006.01) | |
| A61K 31/196 | (2006.01) | |
| A61K 31/365 | (2006.01) | |
| A61K 31/415 | (2006.01) | |
| A61K 31/42 | (2006.01) | |
| A61K 31/444 | (2006.01) | |
| A61P 19/02 | (2006.01) | |
| A61P 29/00 | (2006.01) | |

(52) U.S. Cl.
CPC .......... *A61K 31/737* (2013.01); *A61K 9/0053* (2013.01); *A61K 9/4816* (2013.01); *A61K 31/196* (2013.01); *A61K 31/365* (2013.01); *A61K 31/415* (2013.01); *A61K 31/42* (2013.01); *A61K 31/444* (2013.01); *A61P 19/02* (2018.01); *A61P 29/00* (2018.01)

(58) Field of Classification Search
CPC .. A61K 31/737; A61K 31/196; A61K 31/365; A61K 31/415; A61K 31/42; A61K 31/444; A61K 9/4866; A61K 31/635; A61P 29/00; A61P 19/02; A61P 19/06
See application file for complete search history.

(56) References Cited

U.S. PATENT DOCUMENTS

| | | |
|---|---|---|
| 5,145,841 A | 9/1992 | Cullis-Hill |
| 5,180,715 A | 1/1993 | Parsons |
| 2006/0177504 A1 | 8/2006 | Sundharadas |
| 2011/0251154 A1 | 10/2011 | Stajic |
| 2017/0340561 A1 | 11/2017 | Munjal |

FOREIGN PATENT DOCUMENTS

| | | | |
|---|---|---|---|
| WO | 2002/056878 A2 | 7/2002 | |
| WO | WO-2006097459 A1 * | 9/2006 | ........... A61K 31/415 |
| WO | 2007/071420 A1 | 6/2007 | |
| WO | 2011/050944 A1 | 5/2011 | |
| WO | 2012103588 | 8/2012 | |
| WO | 2015/127416 A1 | 8/2015 | |
| WO | WO-2016191698 A1 * | 12/2016 | ........... A61K 31/737 |

OTHER PUBLICATIONS

Lazzaroni, M., and G. Bianchi Porro. "Gastrointestinal side-effects of traditional non-steroidal anti-inflammatory drugs and new formulations." Alimentary pharmacology & therapeutics 20 (2004): 48-58. (Year: 2004).*
Fda.gov, ELMIRON-100 mg, obtained online at: https://www.accessdata.fda.gov/drugsatfda_docs/label/2008/020193s009lbl.pdf, downloaded on Nov. 16, 2022. (Year: 2002).*
Frampton, J.E., Keating, G.M. Celecoxib. Drugs 67, 2433-2474 (2007). (Year: 2007).*
Ballas, Samir K. "Current issues in sickle cell pain and its management." ASH Education Program Book 2007.1 (2007): 97-105. (Year: 2007).*
International Patent Application No. PCT/AU2019/050119, International Search Report, dated May 16, 2019, 8 pages.
International Patent Application No. PCT/AU2019/050119, Written Opinion of the International Searching Authority, 8 pages.
Afilalo, Jonathan, et al., "Long-term Risk of Ischemic Stroke Associated wit Rofecoxib." Cardiovasc Drugs Ther, 2007, vol. 21, pp. 117-120.
Aungst, Bruce J., "Absorption Enhancers: Applications and Advances." The AAPS Journal, vol. 14, No. 1, Mar. 2012, pp. 10-18.
Cairns, John A., "The Coxibs and Traditional Nonsteroidal Anti-Inflammatory Drugs: A Current Perspective on Cardiovascular Risks." Canadian Journal of Cardiology, vol. 23, No. 2, Feb. 2007, pp. 125-131.

(Continued)

*Primary Examiner* — Abigail Vanhorn
(74) *Attorney, Agent, or Firm* — Fitch, Even, Tabin & Flannery LLP

(57) ABSTRACT

Pharmaceutical and veterinary compositions for oral administration comprising a therapeutically effective amount of at least one coxib together with a therapeutically effective amount of pentosan polysulfate or a pharmaceutically acceptable salt thereof are described. The compositions have application for the prophylaxis or treatment of pain and/or inflammation. There is also described a pharmaceutical or veterinary composition comprising a therapeutically effective amount of at least one coxib. The compositions in at least some forms may be lactose free and/or provided in a non-gelatin capsule. Further, there are provided methods for administration of a therapeutically effective amount of at least one coxib in combination with pentosan polysulfate or a pharmaceutically acceptable salt thereof for the prophylaxis or treatment of pain and/or inflammation.

15 Claims, 2 Drawing Sheets

(56) References Cited

OTHER PUBLICATIONS

Figure 1:
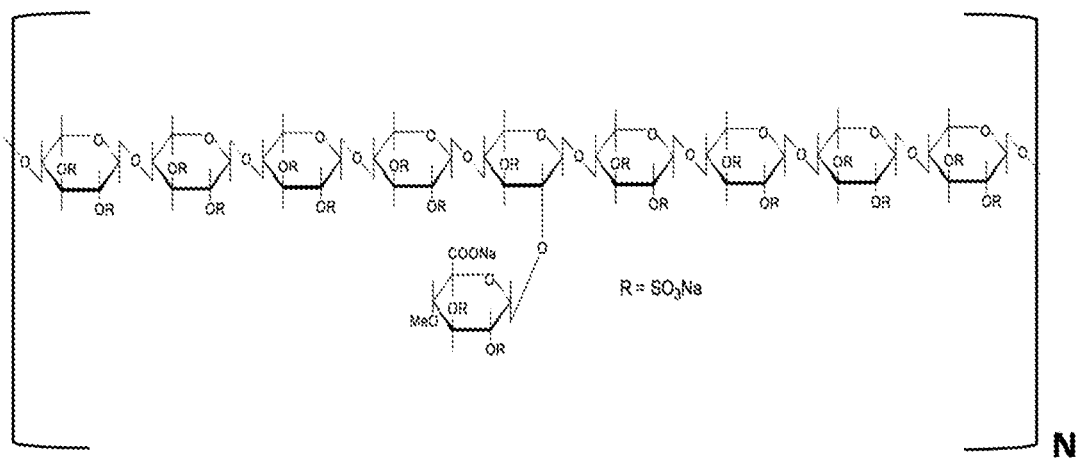

ELMIRON—100g (pentosan polysulfate sodium) Capsules, information sheets—14 pages, Ortho-McNeil-Janssen Pharmaceuticals, Inc., OMJPI 2002, 1998, New Jersey.
ELMIRON Capsules—100g (pentosan polysulfate sodium) information sheets—2 pages, Arthropharm Pty Ltd, Bondi Junction NSW, Australia, TGA approved 1994.
Extended European Search Report for EP 19753718.6, dated Nov. 8, 2021, 10 pages.
Fisher, A.M., et al., "Comparison Between the Effect of Pentosan Polysulfate Heparin and Antithrombin III Injections in Antithrombin III Deficient Patients." Thrombosis Research, vol. 37, 1985, pp. 295-307.
Ghosh, Peter. "The Pathobiology of Osteoarthritis and the Rationale for the Use of Pentosan Polysulfate for Its Treatment." Seminars in Arthritis and Rheumatism, vol. 28, No. 4, Feb. 1999, pp. 211-267.
Kim, Tae-Won, et al., "A Brief Overview of the Coxib Drugs in the Veterinary Field." American Journal of Animal and Veterinary Science, vol. 8, No. 2, 2013, pp. 89-97.
Kohn, Mark D., et al., "Kellgren-Lawrence Classification of Osteoarthritis." Clinical Orthopaedics and Related Research, 2016, vol. 474, pp. 1886-1893.
Kumagai, Kenji, et al., "Sodium Pentosan Polysulfate Resulted in Cartilage Improvement in Knee Osteoarthritis—An Open Clinical Trial." BMC Clinical Pharmacology, 2010, vol. 10, No. 7, 9 pages.
Losonczy, Hajna, et al., "Effects of Various Doses of SP 54 on Fibrinolytic Activity in Patients with Thrombotic Diseases." ISSN 0323-4347, Folia Haematol., Leipzig, 115 (1988) 3, S. pp. 388-393.
Lupia, Enrico, et al., "Pentosan polysulfate inhibits atherosclerosis in Watanabe heritable hyperlipidemic rabbits: differential modulation of metalloproteinase-2 and -9." Laboratory Investigation, 2012, vol. 92, pp. 236-245.
Mill, Deanna, et al., "Managing acute pain in patients who report lactose intolerance: the safety of an old excipient re-examined." Therapeutic Advances in Drug Safety, 2018, vol. 9, No. 5, pp. 227-235.
Prakash, Ajay, et al., "Are your capsules vegetarian or nonvegetarian: An ethical and scientific justification." Indian Journal of Pharmacology, Sep.-Oct. 2017, vol. 49, No. 5, pp. 401-404.
Sakurai-Yamashita, Yasuko, et al., "Neuroprotective effect of pentosan polysulfate on ischemia-related neuronal death of the hippocampus." Neuroscience Letters, vol. 409, 2006, pp. 30-34.
Wu, Jiehua, et al., "Pentsan polysulfate binds to STRO-1+ mesenchymal progenitor cells, is internalized, and modifies gene expression: a novel approach of pre-programing stem cells for the therapeutic application requiring their chondrogenesis." Stem Cell Research & Therapy, 2017, vol. 8:278, pp. 1-15.
Zarghi, Afshin, et al., "Selective COX-2 Inhibitors: A Review of Their Structure-Activity Relationships." Iranian Journal of Pharmaceutical Research, 2011, vol. 10, No. 4, pp. 655-683.
Faaij, R.A., et al., "The Oral Bioavailability of Pentosan Polysulphate Sodium in Healthy Volunteers." Eur J. Clin Pharmacol, 1999, vol. 54, pp. 929-935.
Puljak, Marin A, et al., Celecoxib for Osteoarthritis (Review), Cochrane Database of Systematic Reviews, 2017, Issue 5, pp. 1-143.
Ghosh, Peter, et al., "Effects of Pentosan Polysulfate in Osteoarthritis of the Knee: A Randomized, Double-Blind, Placebo-Controlled Pilot Study." Current Therapeutic Research, vol. 66, No. 6, Nov./Dec. 2005, pp. 552-571.
Anderson, Janet M., et al., "Effects of Pentosan Polysulfate on Peripheral Blood Leukocyte Populations And Mononuclear Cell Procoagulant Activity in Patients with Osteoarthritis" Current Therapeutic Research, vol. 58, No. 2, Feb. 1997, pp. 93-107.
Bobadilla, Norma A., et al., "Pentosan Polysulfate Prevents Glomerular Hypertension and Structural Injury Despite Persisting Hypertension in 5/6 Nephrectomy Rats" Journal of the American Society of Nephrology, vol. 12, 2001, pp. 2080-2087.
Laufer, Stefan. "Discovery and development of ML3000" Inflammopharmacology, vol. 9, No. 1,2, 2001, pp. 101-112.
Ghosh, Peter, et al., "Interactions of Pentosan Polysulfate with Cartilage Matrix Proteins and Synovial Fibroblasts Derived from Patients with Osteoarthritis" Osteoarthritis and Cartilage, vol. 4, 1996, pp. 43-53.
Gong, Li, et al, "Celecoxib Pathways: Pharmacokinetics and Pharmacodynamics" Pharmacogenetics and Genomics, vol. 22, No. 4, Apr. 2012, pp. 310-318.
Lin, Han-Ching, et al., "5-Lipoxygenase Inhibitors Attenuate TNF-α-Induced Inflammation in Human Synovial Fibroblasts" PLOS One, vol. 9, No. 9, Sep. 2014, pp. 1-11.
Martel-Pelletier, J., et al., "Therapeutic Role of Dual Inhibitors of 5-LOX and COX, Selective and Non-selective Non-steroidal Antiinflammatory Drugs" Ann Rheum Dis, vol. 62, 2003, pp. 501-509.
Meirer, Karin, et al, "Inhibitors of the Arachidonic Acid Cascade: Interfering with Multiple Pathways", Basic & Clinical Pharmacology & Toxicology, vol. 114, 2014, pp. 83-91.
Smith, Margaret, et al, "Pentosan Polysulfate Affords Pleotropic Protection to Multiple Cells and Tissues" Pharmaceuticals, vol. 16, No. 437, 2023, pp. 1-33.
Vistnes, Mariam et al., "Pentosan Polysulfate Decreases Myocardial Expression of the Extracellular Matrix Enzyme ADAMTS4 and Improves Cardiac Function In Vivo in Rats Subjected to Pressure Overload by Aortic Banding" PLOS One, vol. 9, No. 3, Mar. 2014, pp. 1-14.
Ghosh, Peter, et al, "Vascular Mechanisms in Osteoarthritis." Best Practice & Research Clinical Rheumatology, vol. 15, No. 5, Dec. 2001, pp. 693-709.
Hata, Aaron, et al., "Pharmacology and Signaling of Prostaglandin Receptors: Multiple Roles in Inflammation and Immune Modulation" Pharmacology & Therapeutics. Aug. 2004, vol. 103, No. 2, pp. 147-166.

* cited by examiner

METHODS AND COMPOSITIONS FOR THE TREATMENT OF PAIN AND/OR INFLAMMATION

FIELD OF THE INVENTION

The present invention relates to pharmacological compositions for the treatment of pain and/or inflammation. Methods for the prophylaxis or treatment of pain and/or inflammation are also provided.

BACKGROUND OF THE INVENTION

Musculoskeletal disorders such as rheumatoid arthritis (RA), osteoarthritis (OA), back and neck pain arising from disc degeneration (DD) or ankylosing spondylosis and osteoporosis (OP) are the major cause of morbidity throughout the world. These diseases have a substantial influence on health and quality of life and inflict an enormous cost on health systems (Scott J C, Hochberg M C. Arthritic and other musculoskeletal diseases, In: Chronic Disease Epidemiology, Brownson R C, Remington P L and Davis J L, eds. Washington, DC. American Public Health Association, 1993). It has been estimated that musculoskeletal diseases cost the Australian community $1.3 billion annually in direct costs and $4.2 billion in indirect costs. This represents 1.3% of GNP (Arthritis Foundation of Australia, Access Economics Pty Ltd report, 2001, March L and Bagga H. Epidemiology of osteoarthritis in Australia, MJA. 2004; 180 Supplement: S6-S10). Population based studies conducted in other developed countries show similar incidence and health burdens to those of Australia. In the United States, for example, it has been estimated that more than 43 million individuals suffer from arthritis with annual costs in terms of their medical care and lost wages being in the order of US$65 billion (Yelin E. The economics of osteoarthritis. In: Brandt K D, Doherty M, Lohmander L S, eds. Osteoarthritis. New York, NY: Oxford Press 2003 ($2^{nd}$ edition):23-30). Moreover, this figure is anticipated to rise substantially as the longevity of the ageing population increases. Indeed, it has been predicted that OA will affect 60 million Americans by the year 2020 and by extrapolation, this number will be several orders of magnitude higher for the Asia-Pacific region (Murati S, Oka H, Atune T, Mabuchi A, En-Yo Y, et al. Prevalence of radiographic knee osteoarthritis and its association with knee pain in elderly Japanese population-based cohorts: The ROAD study. Osteoarthritis and Cart. 2009; 17:1137-1143). Given that more than 210 million Chinese will exceed the age of 65 years by 2027 and the majority will be affected by OA (Nguyen T, Osteoarthritis in Southeast Asia. International J Clinical Rheumatology. 2014; 9:405-408) it can be anticipated that the medical and financial burden of managing of these patients within the Asia pacific region will escalate within the next ten years.

The etiology of OA is multifactorial, with aging, genetic, hormonal and mechanical factors all contributing to varying degrees. OA emerges as a clinical syndrome when these etiological determinants provoke sufficient joint structural damage to cause impairment of function and stimulate symptoms of pain and joint stiffness. The appearance of these symptoms is usually accompanied radiologically by joint space narrowing due to loss of articular cartilage or disc height and extensive re-modelling of subchondral bone with proliferation at the joint margins (osteophytosis) (Altman R, Asch E, Bloch D, Bole G, Bornestein D, Brandt K, et al. Development of criteria for the classification and reporting of osteoarthritis—classification of osteoarthritis of the knee. Arthritis Rheum 1986; 29:1039-49).

As the disease progresses joints are characterized pathologically by extensive cartilage failure, and release of their antigenic break-down products into the synovial space resulting in the establishment of synovial inflammation (Glant T T, Fülöp C, Cs-Szabó G, Buzas E. Ragasa D, Mikecz K. Mapping of arthritogenic/autoimmune epitopes of cartilage aggrecans in proteoglycan-induced arthritis. Scand J Rheumatol 1995; 24:43-9, Smith M D, Triantafillou S, Parker A, Youssef P P, Coleman M. Synovial membrane inflammation and cytokine production in patients with early osteoarthritis. J Rheumatol 1997; 24:365-71.

The presence of synovitis in OA joints has been shown at arthroscopic examination (Lindblad S, Hedfors E. Arthroscopic and immunohistologic characterization of knee joint synovitis in osteoarthritis. Arthritis Rheum 1987; 30:1081-8, Soren A. Osteoarthritis—an arthritis? Z Rheumatol 1982; 41:1-6) and immunohistologically in tissues obtained at the time of joint replacement surgery ((Revell P A, Mayston V, Lalor P, Mapp P. The synovial membrane in osteoarthritis—a histological study including the characterization of the cellular infiltrate present in inflammatory osteoarthritis using monoclonal antibodies. Ann Rheum Dis. 1988; 47:300-7). This synovial inflammation, once established, can alter the metabolism of resident synoviocytes, the cells that are the major biosynthetic source of hyaluronan in synovial fluid. (Balazs E A. The physical properties of synovial fluid and the special role of hyaluronic acid. In: Disorders of the Knee, Helfet A J, ed. Philadelphia. J P Lippincott, 1982, 61-74. Inflammatory mediators released from local mononuclear cells and infiltrating leukocytes including prostaglandins promote increased vascular permeability and elevated levels of plasma in synovial fluid (Pelletier J-P, DiBattista J A, Roughley P, McCollum R, Martel-Pelletier J. Cytokines and inflammation in cartilage degradation. Rheum Dis Clin N Am. 1993; 19:545-68).

As outlined above, the pathology of OA is characterized by the degradation and loss of articular cartilage from weight bearing joint surfaces, subchondral bone necrosis and remodeling together with synovial tissue inflammation. However, since the functions of the respective components of the joint are interdependent, failure of one will inevitably lead to molecular and cellular changes in the others. Because of the cross-talk between all the tissues of the synovial joint it has been difficult to identify precisely where the initial lesions of OA occur, if indeed a single event is responsible for the pathogenesis of this disease.

Rheumatoid Arthritis (RA) is a chronic autoimmune disease whose exact cause is unknown, although genetic and environmental factors are recognised as major contributors (Choy E. Understanding the dynamics: pathways involved in the pathogenesis of rheumatoid arthritis. Rheumatology 2012; 51:v3v11doi:10.1093/rheumatology/kes113). Once established, disease progression is mediated by the complex interactions of neutrophils, T and B cells that differentiate and elaborate pro-inflammatory cytokines, antibodies and prostaglandins (PGs) all of which act both systemically and locally within the synovial joints. In synovial joints the migration of B cells to the synovium and subsynovial tissues is followed by their differentiation into antibody-producing cells, while the recruited T cells undergo differentiation and release pro-inflammatory cytokines including TNF-α, IL-1, IL-6, IL-8, IL-17 and GM-CSF amongst others (Imboden J B. The immune-pathogenesis of rheumatoid arthritis. Annual Rev Pathology. 2009; 4:417-34, McInnes I B, Schett G. The pathogenesis of rheumatoid arthritis. The New England journal of medicine 2011; 365(23):2205-19/, Alunno A, Manetti M, Caterbi S, et al. Altered immuneregulation in rheumatoid arthritis: the role of regulatory T cells and pro-inflammatory th17 cells and therapeutic implications. Mediators of Inflammation. 2015: 751-793).

The resulting synovitis arising from the influx of neutrophils and lymphocytes which, together with the activated resident mononuclear cells, particularly macrophage, release additional cytokines, stimulates hyperplasia, stromal activation and angiogenesis leading to an aggressive tumor-like pannus that erodes the underlying articular cartilage and subchondral bone ((Choy E. Understanding the dynamics: pathways involved in the pathogenesis of rheumatoid arthritis. Rheumatology 2012; 51:v3v11doi:10.1093/rheumatologyikes113, Shimizu T. "Lipid mediators in health and disease: enzymes and receptors as therapeutic targets for the regulation of immunity and inflammation," Annual Review of Pharmacology and Toxicology. 2009; 49: 123-150). Collectively all these mediators orchestrate the ongoing pathobiology of RA Synovial inflammation and joint pain have been the primary therapeutic targets for the first-line management of both OA and RA since the commercial development of Aspirin in the late $19^{th}$ century. The use of aspirin for the treatment of pain and inflammation subsequently led to the development of agents known as non-steroidal anti-inflammatory drugs (NSAIDs). However, it was not until 1971 that the inhibition of the cyclooxygenase (COX) enzyme system was elucidated as a primary site of action of this class of drugs (Vane J R, Botting R M. The mechanism of action of aspirin. Thrombosis Research. 2003; 110: 255-258. Ferreira S H, Moncada S, Vane J R. Prostaglandins and the mechanism of analgesia produced by aspirin-like drugs. British J. Pharmac. 1973; 49:86-97. Flowers R J. Development of COX-2 inhibitors. Nature reviews drug discovery. 2003; 2:191-2003).

The COX enzymes catalyse the biosynthesis of the prostaglandins (PGs) and thromboxane from cell membrane derived arachidonic acid (AA) but the metabolism of AA is also channeled via an alternative route known as the lipoxygenase (LO) pathway which generates the leukotrienes (LT) and lipoxins (Meirer K, Steinhiber D, Proschak E. Inhibitors of the arachidonic cascade: interfering with multiple pathways. Basic Clinical Pharmacology and Toxicology. 2014; 114; 83-91, Hata A N, Breyer B M. Pharmacology and signaling of prostaglandin receptors: multiple roles in inflammation and immune modulation. Pharmacology and Therapeutics. 2004:103:147-166).

The cyclooxygenase enzyme has been shown to exist as two isoforms, COX-1 and COX-2 (Flowers R J. Development of COX-2 inhibitors. Nature Reviews Drug Discovery. 2003; 2:191-2003). Significantly, COX 1 is constitutively expressed in mammalian cells and generates PGE-1. This prostaglandin is implicated a wide variety of physiological activities, including renal function, gastrointestinal protection and platelet aggregation (Vane J R, Botting R M. The mechanism of action of aspirin. Thrombosis Research. 2003; 110: 255-258). COX-2 is not constitutively expressed and its biosynthesis is induced when synovial and inflammatory cells are activated by noxious stimuli such as by bacterial endotoxins, pro-inflammatory cytokines and other ligands (Vane J R, Bating R M. The mechanism of action of aspirin. Thrombosis Research. 2003; 110: 255-258).

The deleterious side effects that were frequently associated with the early chronic use of NSAIDs for the pharmacological management of rheumatic disorders such as OA and RA, particularly on the gastrointestinal tract, kidneys and bone, clearly indicated that they were not acting specifically on COX-2 but were also inhibiting the protective COX-1 enzyme. (Lichtenstein D R, Syngal S, Wolfe M M. Nonsteroidal anti-inflammatory drugs and the gastrointestinal tract. The double-edged sword. Arthritis Rheum. 1995; 38:5-18, Davies M N, Wallace J L. Nonsteroidal anti-inflammatory drug-induced gastrointestinal toxicity. New insights into an old problem. J Gastroenterology. 1997; 32:127-33, Manoukian A V, Carson J L. Nonsteroidal anti-inflammatory drug-induced hepatic disorders. Incidence and prevention. Drug Safety 1996; 15: 64-71.

The knowledge that the COX enzyme existed in two isoforms and that both enzymes were inhibited to varying degrees by the traditional NSAIDs stimulated the search and development of compounds that were specifically designed to inhibit the COX-2 gene product. Subsequent clinical trials in patients with OA, and RA, using these COX-2—specific inhibitors demonstrated they were therapeutically as effective as the conventional NSAIDs in reducing the symptoms of arthritis but the levels of gastric ulcers and mucosal damage were significant reduced (Goldenberg M M. Celecoxib, a selective cyclooxygenase-2 inhibitor for the treatment of rheumatoid arthritis and osteoarthritis. Clin Ther. 1999; 211497-513). In addition, COX-2—specific inhibitors exhibited no effect on platelet aggregation, and did not prolong bleeding time Goldberg loc.cit).

In 1998 the first specific Cox-2 inhibitor, Celebrex™ (celecoxib) was approved by the United States Food & Drug Administration (FDA) and marketed by Pfizer Inc. (New York, NY, USA). One year later Vioxx™ (Rofecoxib) developed by Merck & Co (Kenilworth, NJ, USA) followed. Notwithstanding the advantageous reduction in gastric toxicity observed in using these selective COX-2 inhibitors, increased incidences of major vascular events began to emerge with their chronic application, including stroke, myocardial infarction and deep vein thrombosis. These reports resulted in clinical opinion leaders questioning the safety of the drugs for elderly patients with high blood pressure, or a predisposition to thrombosis and related cardiovascular problems (Gislason G H, Jacobsen S, Rasmussen J N, Rasmussen S, Buch P, Friberg J, Schramm T K, Abildstrom S Z, Kober L, Madsen M, Tom-Pedersen C. Risk of death or reinfarction associated with the use of selective cyclooxygenase-2 inhibitors and nonselective nonsteroidal anti-inflammatory drugs after acute myocardial infarction Circulation. 2006; 113:2906-13. Brophy J M. Celecoxib and cardiovascular risks. Expert Op & Drug Safety. 2005; 6:1005-15, Dajani E Z, Islam K. Cardiovascular and gastrointestinal toxicity of selective cyclooxygenase-2 inhibitors in man. J Physiol Pharmacol. 2008; 59Supp12: 117-33.

As a consequence, Vioxx was withdrawn from the market by Merck in 2004 and in 2005 the FDA released a memorandum summarising their evaluation of 223 cases in the United States of thrombotic or embolic events associated with rofecoxib (99 cases), celecoxib (102 cases), and etodolac (22 cases). The FDA identified adverse effects of these drugs included myocardial infarction, cerebrovascular events, pulmonary embolism and deep venous and miscellaneous thrombotic events. Significantly, the safety report noted that that the majority of cases were for elderly patients who had used the recommended dose of the drugs for managing arthritic pain, with females representing more than 65% of the group. Irrespective of these adverse findings, the use of selective COX-2 specific inhibitors for the management of OA and early stage RA continued to expand with Celebrex (Celecoxib) and its generic forms now providing the most frequently prescribed NSAID by medical practitioners for the early management of pain and inflammation arising from rheumatic diseases and allied conditions such as back pain.

The metabolism of AA mediated via the lipoxygenase (LO) pathway generates the leukotrienes (LT) and lipoxins (Meirer K, Steinhiber D, Proschak E. Inhibitors of the arachidonic cascade: interfering with multiple pathways. Basic Clinical Pharmacology and Toxicology. 2014; 114; 83-91). Leukotrienes not only increase microvascular permeability but are potent chemotactic agents and indirectly reduce the expression of TNF-alpha, a master pro-inflammatory gene product (Han-Ching Lin, Tzu-Hung Lin,Ming Yueh Wu, Yung-Cheng Chiu, Chih-Hsin Tang, et al. 5-Lipoxygenase Inhibitors Attenuate TNF-α-Induced Inflammation in Human Synovial Fibroblasts. PLoS ONE, 2014: e107890. https://doi.org/10.1371/journal.pone. 0107890). Moreover, it has been reported that NSAIDs by blocking the COX mediated pathway may shunt the metabolic cascade of AA to the alternative lipoxygenase route, thereby enhancing the production of leukotrienes such as LTB4 (Laufer S. Discovery and development of ML 3000. Inflammacology. 2001; 9:101 112; Martel-Pelletier J, Lajeunesse D, Rebould P, Pelletier J-P. Ann Rheum Dis. 2003; 62: 501-509).

It is believed there are no reports that selective COX-2 inhibitors, such as Celebrex™ (celecoxib), can also inhibit the production of leukotrienes (Gong L, Thorn C F, Bertagnolli M M, Grosser T, et al, Celecoxib pathways; pharmacokinetics and pharmacodynamics. Pharmacogenetics and Genomics. 2012; 22: 310-318). On the contrary, they may exacerbate the levels of these inflammatory mediators. In view of this deficiency investigators have sought to develop drugs for application in inflammatory diseases, that were capable of inhibiting both 5-lipoxygenase and cyclooxygenases pathways of AA metabolism (Laufer S. Discovery and development of ML 3000. Inflammacology. 2001; 9: 101-112, Martel-Pelletier J, Lajeunesse D, Reboul P, Pelletier J-P. Therapeutic role of dual inhibitors of 5-LOX and COX, selective and non-selective non-steroidal anti-inflammatory drugs Ann Rheum Dis. 2003; 62: 501-509).

SUMMARY OF THE INVENTION

The present invention relates to the use of at least one coxib for specifically inhibiting the COX-2 enzyme system in combination with pentosan polysulfate (PPS) for inhibiting the alternate Lipoxygenase (LO) pathway of arachidonic acid (AA) metabolism. Pentosan polysulfate advantageously exhibits anti-thrombotic and other useful pharmacological activities not possessed by coxibs, and the use of PPS may also offset the known risk factors associated with the use of coxibs in elderly patients that may be pre-disposed to thrombosis, stroke or other cardiovascular events. PPS, however, is well known to have very low oral bioavailability and so has conventionally been administered parenterally. The invention, however, in at least some embodiments stems at least in part from the surprising observation that PPS administered orally in combination with a coxib can be highly effective in attenuating joint pain and joint stiffness.

In particular, in an aspect of the invention there is provided a pharmaceutical or veterinary composition for oral administration comprising a therapeutically effective amount of at least one coxib and a therapeutically effective amount of pentosan polysulfate or a pharmaceutically acceptable salt thereof.

In another aspect of the invention there is provided a method for the prophylaxis or treatment of pain and/or inflammation in a mammal, comprising administering to the mammal an effective amount of at least one coxib in combination with an effective amount of pentosan polysulfate or a pharmaceutically acceptable salt thereof.

Typically, in a method as described herein a composition embodied by the invention is administered to the mammal.

In at least some embodiments, the pain and/or inflammation can, for instance, arise from a rheumatic disease or condition such as arthritis (e.g., osteoarthritis or rheumatoid arthritis), soft tissue injuries and related disorders. Accordingly, compositions as described herein have particular application to treatment of these conditions.

Any coxib suitable for the intended purpose of the composition can be utilised in the composition.

Typically, the pentosan polysulfate is in the form of physiologically acceptable salt.

Typically, a composition embodied by the invention further comprises a physiologically acceptable carrier suitable for oral administration.

In at least some embodiments, a composition embodied by the invention can be in unit dosage form.

Typically, a composition in accordance with the invention is a solid composition although liquid formulations of the composition are also expressly encompassed herein.

In another aspect of the invention there is provided a pharmaceutical or veterinary composition comprising a therapeutically effective amount of at least one coxib and a therapeutically effective amount of pentosan polysulfate or a physiologically acceptable salt thereof, for use in the prophylaxis or treatment of pain and/or inflammation in a mammal.

In another aspect of the invention there is provided a pharmaceutical or veterinary composition comprising a therapeutically effective amount of at least one coxib and a therapeutically effective amount of pentosan polysulfate or a physiologically acceptable salt thereof, for use in the prophylaxis or treatment of a rheumatic disease or condition in a mammal.

In another aspect there is provided a method for treating a rheumatic disease or condition in a mammal, comprising administering to the mammal a composition embodied by the invention.

In another aspect of the invention there is provided a method for treating pain associated with inflammation in a mammal, comprising administering to the mammal a therapeutically effective amount of at least one coxib in combination with a therapeutically effective amount of pentosan polysulfate or a pharmaceutically acceptable salt thereof.

In another aspect of the invention there is provided a method for prophylaxis or treatment of pain and/or inflammation in a mammal, comprising administering to the mammal an effective amount of at least one coxib in combination with a therapeutically effective amount of pentosan polysulfate or a pharmaceutically acceptable salt thereof.

Typically, a composition embodied by the invention will exclude a penetration enhancer for increasing the bioavailability of the PPS as described herein. Likewise, in methods as described herein, the PPS will typically be administered in combination with at least one coxib in the absence of the administration of at least one penetration enhancer as defined herein for increasing the bioavailability of the PPS.

Typically, a composition embodied by the invention will exclude lactose. Surprisingly, the inventors have also found that excluding lactose may improve the efficiency and tolerability of both a PPS containing composition in accordance with the invention and the coxib itself when administered alone in a comparator control formulation as further described herein.

Further, typically, composition and dosage forms embodied by the invention are essentially free of gelatin.

In another aspect there is provided herein a pharmaceutical or veterinary composition comprising a therapeutically effective amount of at least one coxib and a therapeutically effective amount of pentosan polysulfate or a pharmaceutically acceptable salt thereof, wherein the composition does not contain lactose.

Still further, there is provided herein a pharmaceutical or veterinary composition comprising a therapeutically effective amount of at least one coxib together with a physiologically acceptable carrier or excipient(s), wherein the composition does not contain lactose.

In another aspect there is provided a method for prophylaxis or treatment of pain and/or inflammation in a mammal, comprising administering to the mammal an effective amount of at least one coxib in combination with a therapeutically effective amount of pentosan polysulfate or a pharmaceutically acceptable salt thereof, in the absence of administration of lactose for said prophylaxis or treatment.

In another aspect there is provided a method for reducing medical risk associated with administering at least one coxib to a patient, the method comprising administering the coxib to the patient in combination with a therapeutically effective amount of pentosan polysulfate or a pharmaceutically acceptable salt of pentosan polysulfate.

Typically, in this embodiment, the PPS is administered in combination with the at least one coxib for prophylaxis of a cardiovascular disease or condition. The patient in this embodiment (e.g., an elderly patient) may have, or be predisposed to, the cardiovascular disease or condition. Hence, "prophylaxis" includes reducing the risk of exacerbating or acquiring the cardiovascular disease or condition. The reduction of the risk may be essentially avoiding the risk of exacerbation or acquisition of the cardiovascular disease or condition. Typically, the cardiovascular disease or condition is selected from thrombosis, atherosclerosis and ischemia, and cardiovascular diseases and conditions involving one or more of thrombosis, atherosclerosis and ischemia. (e.g., stroke, myocardial infarction, and deep vein thrombosis (DVT)).

In another aspect there is provided a method for prophylaxis or treatment of pain and/or inflammation in a mammal, comprising administering to the mammal an effective amount of at least one coxib in a composition essentially free of lactose.

In another aspect of the invention there is provided the use of at least one coxib in combination with pentosan polysulfate for the prophylaxis or treatment of pain and/or inflammation in a mammal.

In still another aspect of the invention there is provide the use of at least one coxib and pentosan polysulfate in the manufacture of a medicament for the prophylaxis or treatment of pain and/or inflammation in a mammal.

As will be understood, in at least some embodiments of the invention the mammal is a human. In other embodiments the mammal is a non-human animal and the invention extends to veterinary compositions.

Providing at least one coxib and the pentosan polysulfate together in the one orally acceptable composition for administration via the oral route as described herein facilitates ease of administration and compliance with treatment regimens. More particularly, the finding that pentosan polysulfate can be administered orally in combination with at least one coxib allows the combination therapy to be administered without the need for injection. Administration of the combination therapy orally also allows for the at least one coxib and the pentosan polysulfate to be conveniently added to food or water for consumption by an animal to effect treatment.

Advantageously also, one or more embodiments of the invention may provide for pain and/or inflammation such as associated with forms of arthritis and other soft tissue and musculoskeletal injuries to be alleviated. In human terms, this may lead to an improved quality of life of the patient as may be measured by amelioration of symptoms associated with the (e.g., arthritic) disorder, reduced suffering or incapacitation due to presence of the pain, improved joint function, increased mobility and quality of life.

The adverse cardiovascular related events associated with the administration of coxibs to elderly patients and other patients predisposed to high blood pressure and thrombosis has excluded or restricted their use in such patients for ongoing prophylaxis or treatment purposes. Given that PPS advantageously exhibits anti-thrombotic and other useful pharmacological activities not possessed by coxibs, and that the use of PPS may offset the well known risk factors and toxicities associated with the use of coxibs, the present invention in one or more embodiments may allow for the prophylaxis or treatment of such patients for pain, arthritic conditions and other conditions for which coxibs have application whilst reducing the risk of such medical complications.

Further, in at least embodiments, reliance on non-selective non-steroidal anti-inflammatory drugs (NSAIDs) (e.g., ibuprofen, naproxen, and diclofenac), corticosteroids (e.g., Prednisolone) or daily use of non-opioid analgesics such as Acetaminophen (Panadol™, Panadol-Osteo™) or opioid analgesics (e.g., Codeine, Buprenororphine, Dextroproxphene, Fentanyl, Oxycodone, Tapentadol, Tramadol), or combinations of analgesics and NSAIDs may also be reduced or avoided, limiting their adverse pharmacological and addictive side effects. Prolonged use of non-selective NSAIDS, for example, is well known to be associated with gastrointestinal ulcers kidney and liver conditions. More recently, it has been revealed that the increasing use of opioid and/or non-opioid analgesics for controlling pain can be addictive and has become a burgeoning socio-economic problem of present day prescribing practices (Helmerhorst G T, Teunis T, Janssen S J, Ring D. An epidemic of the use, misuse and overdose of opioids and deaths due to overdose, in the United States and Canada: is Europe next? Bone Joint J. 2017; 99B: 856-64, Karanges E A, Blanch B, Buckley N A, Pearson S-A. Twenty-five years of prescription opioid use in Australia: a whole-of-population analysis using pharmaceutical claims. Br J Clin Pharmacol. 2016; 82(1):255-67).

In terms of veterinary use, compositions and combination therapies embodied by the invention include application for the treatment of pain arising from musculoskeletal disorders in horses and companion animals.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers, integers or steps.

Any discussion of documents, acts, materials, devices, articles or the like that has been included in this specification is solely for the purpose of providing a context for the invention. It is not to be taken as an admission that any, or all, of these matters form part of the prior art base or were common general knowledge in the field relevant to the invention as it existed in Australia or elsewhere before the priority date of this application.

The features and advantages of the present invention will become further apparent from the following detailed description of exemplary embodiments of the invention together with the accompanying drawings.

BRIEF DESCRIPTION OF THE
ACCOMPANYING DRAWING(S)

FIG. 1: Structural formula of an example of a repeating unit of a poly-dispersed pentosan polysulfate sodium salt. On average, a single ester sulfated 4-O-methyl-glucopyranosyluronic acid ring is attached laterally via an oxygen linkage to the 2 position of every 9-10$^{th}$ xylanopyranose unit of the polymer. From the molecular weight distribution of 1800-17,000 Da determined by size exclusion chromatography (Jacobsson O, Kuver T, Granath K, Characterization of xylan sulphate by size exclusion chromatography. J Liquid Chromatography. 1986; 9: 1541-1561), the range of polymerization (N) can be estimated as 0.5-6.0. R=$SO_3$Na. Hydrogen attachments are represented by the vertical lines.

Figure 2:
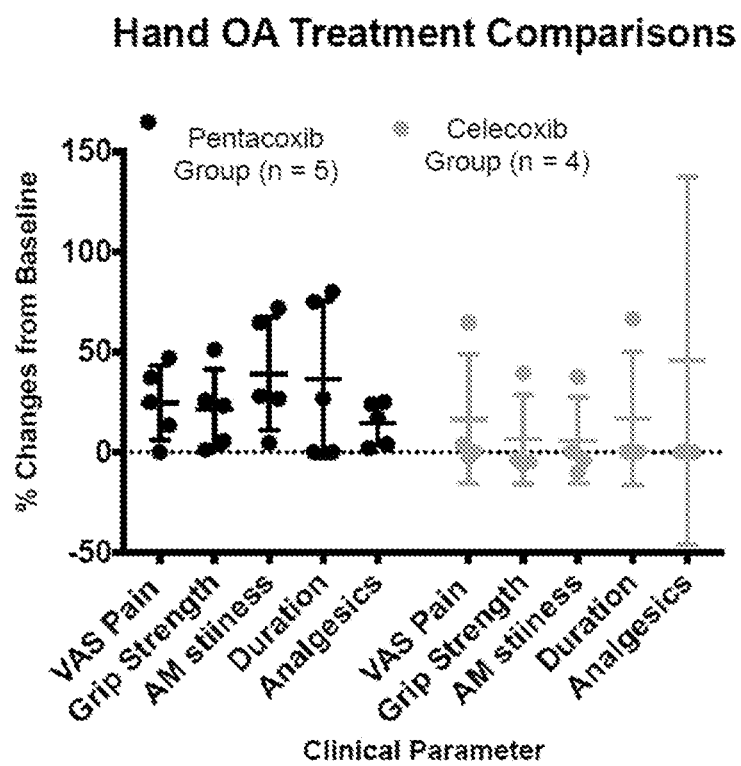

FIG. 2: Graphical representation of the % change in clinically determined visual analogue (VAS) pain scores, grip strength, and duration of joint stiffness recorded before and at termination of the comparator trial for patients with Hand OA. The individual numbers of analgesics or NSAIDs consumed over this period is also shown. The black circles correspond to the values from individual patients assigned to the Pentabrex™ treated group. The black horizontal bars correspond to the group mean value +/− SD for each of the measured clinical parameters. The grey circles and bars correspond to the same measures for the Celecoxib treated group. Circle values that fall below the y-axis of 0.0% indicate that the patients' symptoms were worse after completing the trial. Two-way ANOVA of the data using Graphpad Prism 7.0d software (La Jolla, California, USA) failed to demonstrate significance differences between the two treatment groups. However, as is evident from this figure, the mean values for the individual clinical parameter determined for the Pentbrex™ treated group were higher than the for the celecoxib treated group indicating a greater response to treatment.

Figure 3:
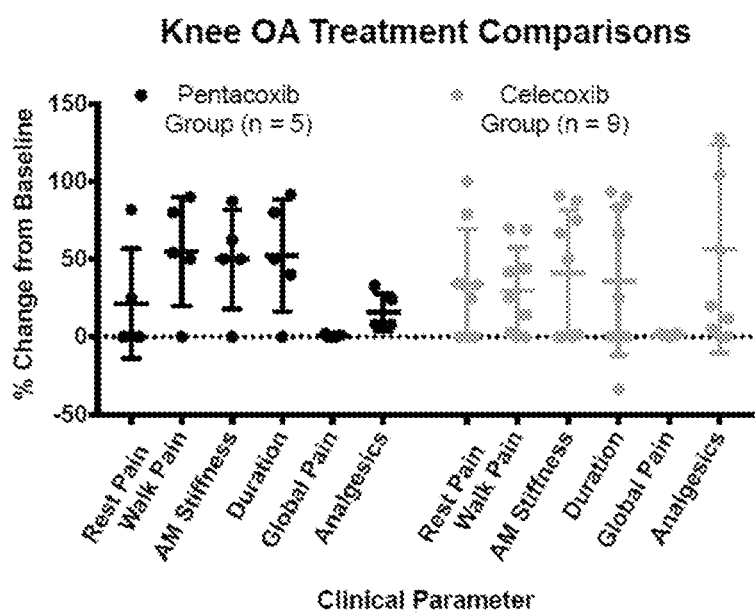

FIG. 3: Graphical representation of the % change in clinically determined visual analogue (VAS) pain scores, grip strength, and duration of joint stiffness recorded before and at termination of the comparator trial for patients with Knee OA. The individual numbers of analgesics or NSAIDs consumed over this period is also shown. The black circles correspond to the values from individual patients assigned to the Pentabrex™ treated group. The black horizontal bars correspond to the group mean value +/− SD for each of the measured clinical parameters. The grey circles and bars correspond to the same measures for the Celecoxib treated group. Circle values that fall below the y-axis of 0.0% indicate that the patients' symptoms were worse after completing the trial. Two-way ANOVA of the data using Graphpad Prism 7.0d software (La Jolla, California, USA) failed to demonstrate significance differences between the two treatment groups due to the limit number of patients recruited for the trial. However, as is evident from this figure the mean values for the individual clinical parameter determined for the Pentabrex™ group were higher than the for the Celecoxib group indicating a greater response to treatment. Moreover, the consumption of additional analgesics and/or NSAIDS by patients in the Celecoxib group during the course of the study was higher than for the Pentabrex™ treated group suggesting the need for additional pain relief for this group.

DETAILED DESCRIPTION OF EXEMPLARY
EMBODIMENTS OF THE INVENTION

By "coxib" as used herein is meant a COX-2 selective nonsteroidal anti-inflammatory drug (NSAID) (see e.g., McMurrey R W, Hardy K J, Cox-2 Inhibitors: today and tomorrow. The American J Med Science. 2002; 323:181-189). The coxib(s) utilised in a composition or method in accordance with the invention can be any coxib(s) suitable for oral administration for prophylatic and/or therapeutic treatment as described herein. Celecoxib (4-[5-(4-methylphenyl)-3-(trifluoromethyl)pyrazol-1-yl] benzene sulfonamide; Chemical Abstracts Sew. Reg. No: 169590-42-5; Celebrex™, G.D Searl LLC, Pfizer Inc, New York, NY, USA, is particularly preferred for use in compositions and methods embodied by the invention although other coxibs that may be utilised can, for instance, be selected from the group consisting of, parecoxib (N-{[4-(5-methyl-3-phenylisoxazole-4-yl)phenyl]sulfonyl}propanamide; CAS No: 198470-84-7); etoricoxib (5-chloro-6'-methyl-3-[4-(methylsulfonyl)phenyl]-2,3'-bipyridine; CAS No: 202409-33-4), lumiracoxib ({2-[(2-chloro-6-fluorophenyl)amino]-5-methylphenyl}acetic acid; CAS No: 220991-20-8), and firocoxib 3-(cyclopropylmethoxy)-5,5-dimethyl-4-(4-methylsulfonylphenyl)furan-2-one; CAS No: 189954-96-9). Firocoxib has particular use in veterinary compositions and especially in the treatment of dogs and horses in accordance with the invention.

Further coxibs that may be utilised in compositions and methods embodied by the invention include rofecoxib™ 4-(4-methylsulfonylphenyl)-3-phenyl-5H-furan-2-one; CAS No: 162011-90-7) and valdecoxib™ 4-(5-methyl-3-phenylisoxazol-4-yl)benzenesulfonamide; CAS No: 181695-72-7). Whilst these coxibs have been associated with adverse cardiovascular events in some patient classes (e.g., elderly patients with higher risk of coronary events) they may nevertheless have application in short term treatments or treatment of particular conditions as described herein under appropriate supervision.

Pentosan polysulfate ([2R,3R,4S,5R)-2-hydroxy-5-[(2S, 3R,4S,5R)-5-hydroxy-3,4-disulfo-oxyoxan-2-yl]oxy-3-sulfooxyoxan-4-yl] hydrogen sulfate) (see chemical structure shown in FIG. 1; CAS No: 37319-17-8; 140207-93-8) (PPS)) is manufactured from Beech wood (*Fagus sylvatica*) hemicellulose by sulfate esterification of the sugar ring hydroxyl groups. It is commonly prepared as the sodium salt (see e.g., CAS No 1300-72-7; Australian Government Department of Health, National Industrial Chemicals Notification and Assessment Scheme) and generally has a weight average molecular weight (MW) of about 5700 Da and a sulfur content of ~16-17% (Ghosh P, Smith M, Wells C. Second line agents in osteoarthritis. In: Dixon J S, Furst D E, eds. Second-Line Agents in the Treatment of Rheumatic Diseases. New York, NY: Dekker; 1992:363-427), and has been used as a thrombo-prophylactic and anti-lipidemic agent since the late 1950s (Halse T. Activation of fibrinolysis and thrombolysis by polysaccharide sulfuric acid esters (heparin, heparinoid) [in German]. Arzneimittelforschung. 1962; 12:574-582).

The scientific literature accumulated over that time has indicated that PPS mobilizes vascular occlusions by promoting fibrinolysis, reducing fibrinogenesis, as well as clearing plasma fats and lipids by promoting release of lipases from the vascular endothelium (Ghosh P, Smith M, Wells C. Second line agents in osteoarthritis. In: Dixon J S, Furst D E, eds. Second-Line Agents in the Treatment of Rheumatic Diseases. New York, NY: Dekker; 1992:363-427). Intravascular lipid and thrombi have been reported to be frequently present in the arterial and venous microvasculature of heads of femur removed at the time of total joint replacement surgery for OA (Bullough P G, DiCarlo E F. Subchondral avascular necrosis: A common cause of arthritis. Ann Rheum Dis. 1990; 49: 412-420, Cheras P A, Freemont A J, Sikorski J M. Intraosseous thrombosis in ischemic necrosis of bone and osteoarthritis. Osteoarthritis Cartilage. 1993; 1: 219-232).

The anti-lipidemic and pro-fibrinolytic effects of sodium-PPS (NaPPS) have been reported in a group of postmenopausal women with mild to moderate osteoarthritis (OA) (Anderson J M, Edelman J, Ghosh P: Effects of pentosan polysulfate on peripheral blood leukocyte populations and mononuclear cell procoagulant activity in patients with osteoarthritis. Curr Ther Res Clin Exp. 1997; 58:93-107). In the study, lipolytic parameters were monitored before drug treatment and 8 and 24 hours after the patients received the first of 4 weekly intramuscular (IM) injections of 3 mg/kg NaPPS. Plasma concentrations of lipoprotein lipase, hepatolipase, and superoxide dismutase were significantly elevated between 2 and 4 hours after drug administration. NaPPS treatment was associated with modifications in peripheral blood mononuclear cell procoagulant activity (MPA) and differential leukocyte counts. Patients' MPA, which before drug treatment was higher than in non-OA controls, was significantly reduced to within the normal range 24 hours after NaPPS administration. These pharmacological effects were maintained for 4 weeks after cessation of administration of the drug (Anderson J M, Edelman J, Ghosh P: Effects of pentosan polysulfate on peripheral blood leukocyte populations and mononuclear cell procoagulant activity in patients with osteoarthritis. Current Ther Res Clin Exp. 1997; 58:93-107). Moreover, of the patients with OA enrolled in the study, 11 reported significant clinical improvement of their symptoms for up to 12 weeks after the last injection (Edelman J, Anderson J, Ghosh P. Disease modification in osteoarthritis: relationship of macrophage procoagulant activity and haematological parameters to symptoms in patients receiving pentosan polysulfate. Osteoarthritis Cart. 1996; 4Suppl: iv-v).

In an earlier hematological study, 15 elderly subjects (5 males, 10 females, mean age 81±10 years) with high blood viscosity and filterability showed significant reduction of these parameters by IM administration of 50 mg NaPPS twice daily for a week (Freyburger G, Larrue F, Manciet G, et al. Hemorheological changes in elderly subjects—effects of pentosan polysulfate and possible role of leucocyte arachidonic acid metabolism. Thromb Haemost. 1987; 57:322-325). As part of the study, the metabolism of $^{14}$C-arachidonic acid cultured with leukocytes isolated from the blood of these patients was also monitored. Seven days after NaPPS administration, the concentrations of arachidonic acid-derived lipoxygenase (LOX) metabolites released from the cells were significantly decreased compared to leukocytes collected before administration of the drug. Interestingly, prostaglandin metabolites generated by the COX pathways were increased but since the blood leukocytes collected for the study were non-stimulated, it is likely that this was the product of the constitutive enzyme, COX-1 (Skelly M M, Hawkey C J. COX-LOX inhibition: Current evidence for an emerging new therapy. Int J Clin Pract. 2003; 57:301-304).

The reduced levels of 5-LOX derived metabolites produced by leukocytes in patients treated with NaPPS were identified by HPLC as the leukotrienes, 5-SHETE, diHETEs, and LTB4. LTB4 in particularly is a potent proinflammatory mediator that can stimulate neutrophil adhesion, chemotaxis, and degranulation (Henderson W R Jr. The role of leukotrienes in inflammation. Ann Intern Med. 1994; 121:684-697). Moreover, LTB4 can induce the synthesis of interleukin 8 and platelet-activating factor, which are known contributors to the inflammatory process. In addition to their pro-inflammatory effects, leukotrienes also directly promote vasoconstriction and vascular permeability (Henderson W R Jr. The role of leukotrienes in inflammation. Ann Intern Med. 1994; 121:684-697, Meirer K, Steinhiber D, Proschak E. Inhibitors of the arachidonic cascade: interfering with multiple pathways. Basic Clinical Pharmacology and Toxicology. 2014; 114; 83-91).

The anti-inflammatory activity of NaPPS has been known since the early studies of Kalbhen et al. (Kalbhen D A. The biochemical and pharmacological basis of the anti-phlogistic/antirheumatic effect of pentosan polysulphate [in German]. Wien Klin Wochenschr. 1978; 90:101-105) who suggested that this activity was largely mediated by the ability of the drug to restabilize "leaky" peripheral vasculature and improve microcirculation in the tissues of affected joints.

The anti-complement activity of PPS and the reduction in humoral mediators of inflammation were later reported in 16 patients with hypercomplementemia (Berthoux F C, Freyria A M, Traeger J. Anticomplement activity of a polyanion: Pentosan sulfate polyester. III. Mechanism of functional inactivation of the different properdin and complement system fractions. Pathol Biol (Paris). 1977; 25:179-184).

Results from further numerous in vitro and animal studies using the sodium and calcium salts of PPS have led to the proposal that these agents might be classified as a disease modifying osteoarthritis drug (DMOAD) because of their ability to diminish the levels of pro-inflammatory mediators (e.g., TNF-alpha), preserve the integrity of the articular cartilage and bone while improving the molecular weight and levels of the joint synovial fluid hyaluronic acid in arthritic joints (Ghosh P. The pathobiology of osteoarthritis and the rationale for the use of pentosan polysulfate for its treatment. Semin Arthritis Rheum. 1999; 28:211-267). 2005; 66:552-571, Sunaga T, Oh N, Hosoya K, Takagi S, Okumura M. Inhibitory effects of pentosane polysulfate sodium on MAP-kinase pathway and NF-κB nuclear translocation in canine chondrocytes in vitro. J Vet Med Sci Jpn Soc Vet Sci. 2012; 74:707-11, Busch S J, et al. Trans-Repressor Activity of nuclear Glycosaminoglycans on Fos and Jun/AP-! Oncoprotein-mediated transcription. J Cell Biology. 1992; 116: 31-42). Although some of the anti-catabolic activities of PPS have been shown to occur via the direct inhibition of enzymes, in particular, elastase and cathepsin-B (Burkhardt D and Ghosh P. Laboratory evaluation of antiarthritic agents as potential chondroprotective agents. Semin Arthritis Rheum. 1987; 17(Suppl 1):3-34), PPS has been reported to directly protect cartilage degradation by inhibiting the aggrecanases ADAMTS-4 and 5 (Troeberg L, Fushimi K, Khokha R, Emonard H, Ghosh P, Nagase H. Pentosan polysulfate is a multi-faceted exosite inhibitor of aggrecanases. FASEB Journal. 2008; 35: 15-24. 2008, Takizawa M, Yatabe T, Okada A, Chijiwa M, Mochizuki S, Ghosh P, Okada Y. Calcium pentosan polysulfate inhibits enzymatic activity of ADAMSTS-4 (aggrecanase-1) from chondrocytes derived from osteoarthritic joints. FEBS Letters. 2008; 582: 2945-2049), and to enhance levels of their endogenous inhibitor, TIMP-3 (Troeberg L, Mulloy B, Ghosh P, Lee M-H, Murphy G, Nagase H. Pentosan polysulfate increases affinity between ADAMTS-5 and TIMP-3 through formation of an electrostatically driven trimolecular complex. Biochem J. 2012; 443: 307-15). Furthermore, PPS enters chondrocytes and fibroblasts where it binds to promoter proteins in their nuclei and down regulates gene expression of matrix metalloproteinases (Ghosh P. The pathobiology of osteoarthritis and the rationale for the use of pentosan polysulfate for its treatment. Semin Arthritis Rheum. 1999; 28:211-267). These chondroprotective activities of NaPPS and CaPPS have been demonstrated to be effective in rat, rabbit, and canine models of OA (Ghosh P. The pathobiology of osteoarthritis and the rationale for the use of pentosan polysulfate for its treatment. Semin Arthritis Rheum. 1999; 28: 211-267).

As follow-up to the encouraging preclinical studies described above, a double blind clinical trial was undertaken in 114 elderly patients (mean age 63±1.5 years) (83 women, 31 men) to determine its safety and efficacy for the management of symptomatic knee OA (Ghosh P, Edelman J, March L, Smith M. Effects of pentosan polysulfate in osteoarthritis of the knee: a randomized, double-blind placebo controlled pilot study. Current Therapeutic research. 2005; 66:552-571). In this study, patients were randomly assigned to receive NaPPS 3 mg/kg or Ringers solution (control) IM for 4 weeks. Efficacy was assessed at enrollment and over the 4 weeks of treatment and at weeks 8, 12, 16, and 24 there after using validated clinical instruments. Safety and tolerability were monitored by blood hematology and biochemical analysis plus patients reported adverse side effects. The results of this study demonstrated that 4 weekly IM injections of NaPPS provided significantly improvement of joint pain at rest relative to placebo controls that was maintained for 20 weeks after the cessation of treatment. In addition, the reduction in pain on walking and other physical activities, such as stair climbing was significantly improved.

The above double-blind study was followed by an open clinical study using 20 Japanese patients with mild knee OA who received weekly subcutaneous injections of 2 mg/kg NaPPS over 6 weeks. Patients were assessed at entry, and on 1, 8, 11, 15, 24 and 52 weeks thereafter. Joint swelling, knee flexion and pain while walking, pain and stair climbing were improved significantly over the period of the study (Kumagai K, Shirabe S, Miyata N, Murata M, Yamauchi A. Sodium pentosan polysulfate resulted in cartilage improvement in knee osteoarthritis—An open clinical trial. BMC Clinical Pharmacology. 2010, 10; 7 http://www.biomedcentral.com/1472-6904/10/7).

In all the above cited clinical studies where PPS was used for the treatment of inflammatory and arthritic disorders the drug was administered systemically via the intra-venous, intra-muscular, intra-articular or sub-cutaneous routes. The selection of the parenteral routes of administration for these medical conditions was considered mandatory in view of the known low bio-availability of PPS when administered via the oral route (Faaij R A, Srivastava N T. van Griensven J M Y, Schoemaker R C, Kluft C et al. The oral bioavailability of pentosan polysulphate sodium in healthy volunteers. Eur J Clin Pharmacol (1999) 54: 929-935; Simon M, McClanahan R H, Shah J F, Repko T, Modi N B. Metabolism of [$^3$H]-pentosan polysulfate sodium (PPS) in healthy human volunteers. Xenobiotica. 2005; 35:775-84). In the latter of those two studies, two groups of eight healthy female subjects were used. One group received a single oral dose of 200 microCi [3H]PPS supplemented with 300 mg un-labelled PPS, the other 300 microCi [3H]PPS supplemented with 450 mg un-labelled PPS. Samples collected over 24 hours were analysed employing radiochromatographic fractioning techniques revealed that 84% of the administered PPS dose was excreted in the faeces as intact PPS, and a smaller percentage (6%) was excreted in urine in a depolymerized form. The presence of small amounts of PPS in the urine of these volunteers may provide an explanation for the reported clinical benefit of long-term oral administration of 300-400 mg PPS daily for the management of interstitial cystitis (Teichman J M H, The role of Pentosan polysulfate in treatment approaches for interstitial cystitis. Urology. 2002; 4(Suppl 1): S21-S27).

Although the administration of PPS via subcutaneous, intramuscular or intra-articular injections was considered necessary to achieve optimum blood and tissue levels of the drug, these routes of administration, irrespective of the agent to be administered, are not benign procedures, since they have been associated with local bleeding, the introduction of opportunistic infections, tissue atrophy and the production of local pain and discomfort at the site of injection (Holland C, Jaeger L, Smentkowski U, Weber B, Otto C. Septic and Aseptic Complications of Corticosteroid Injections: An Assessment. Dtsch Arztebl Int. 2012; 109: 425-30. Tashiro T, et al. Oral administration of polymer hyaluronic acid alleviates symptoms of knee osteoarthritis: a double blind placebo controlled study over a 12 month period. The Scientific World J. 2012. Doi:2012/167928).

To address the problem of the low oral bio-availability of PPS, Parsons et al, proposed co-administration of PPS with penetration enhancers (Parsons C L, Goldberg M, Meenan C P. WO 2015/127416 A1; 2015, the contents of which is incorporated herein in its entirety by cross-reference). A focus of that patent application was the administration of the penetration enhancers with PPS for the managements of interstitial cystitis (IC) related urological disorders. It is claimed in that patent application that the compositions containing PPS with penetration enhancers facilitated the administration of the PPS at lower dosage to achieve successful treatment of IC thereby reducing the frequency and severity of PPS adverse side effects associated with high PPS dosages when used in this and other indications.

As described in WO 2015/127416 (see e.g., paragraph [0019]), the reasons for the poor bioavailability of PPS includes the presence of multiple charged sulfate moieties in the PPS molecule which are well known to present significant difficulty to penetration of the epithelial membrane of the gastro-intestinal tract and the lipid bilayer of the cell membrane. Further, the relatively large molecular size of PPS exacerbates this problem and contributes to its low bioavailability. Penetration enhancers (also known as absorption enhancers) as utilised in WO 2015/127416 are functional excipients included in formulations to improve the absorption of a pharmacologically active drug and typically refers to an agent whose function is to increase penetration/absorption of the drug by enhancing membrane permeation, rather than increasing solubility of the drug (see e.g., Aungst B J, Absorption Enhancers: Applications and Advances. The AAPS Journal, March 2012, Vol. 14, No. 1, 10-18).

In view of the prevailing literature on the low oral bioavailability of PPS the present inventors were therefore surprised to discover that oral administration of a formulation comprising Celecoxib™ and PPS at low dosage and in the absence of the inclusion of penetration enhancer(s) in the formulation (Pentacoxib™, Pentabrex™, Proteobioactives Pty Ltd, Balgowlah, NSW, Australia) either daily or 2-4 times a week to arthritic patients, was effective in attenuating the symptoms of their pain and joint stiffness arising from this disease. This finding was even more surprising since the OA patients who volunteered to participate in the clinical studies were known not to have had their symptoms resolved by the use of conventional NSAIDs, including celecoxib.

Further, the above outcomes were obtained in the absence of the administration of any penetration enhancer(s) to the patients to increase the bioavailability of the PPS. Penetration enhancers are themselves chemical compounds and so potentially, can have unknown or undesirable effects on a patient. Typically then, penetration enhancers as (e.g., as described in WO 2015/127416) for increasing the bioavailability of the PPS are excluded from methods, compositions and formulations of a PPS and a coxib in accordance with embodiments of the present invention.

In the context of the present invention, the term "penetration enhancer" as used herein is to be taken to encompass a functional excipient, or a combination of excipients, provided in an amount, and whose function is, to increase the bioavailability of PPS by enhancing biological membrane penetration of the PPS when the PPS is administered orally in accordance with the invention.

Typically, the amount of the penetration enhancer(s) for increasing the bioavailability of the PPS is from about 50 mg to about 800 mg per unit dose of the composition comprising the PPS and at least one coxib as described herein, from about 100 mg to about 500 mg per unit dose of the composition, or from about 150 mg to about 400 mg per unit dose of the composition.

As another or alternative measure, the amount of the penetration enhancer(s) for increasing the bioavailability of the PPS in a unit dose of the composition comprising the PPS and the at least one coxib as described herein is in a ratio, by weight of the penetration enhancer to the PPS, of from about 0.167:1 to about 8:1, or from about 0.50:1 to about 3:1, or from about 0.75:1 to about 2:1.

As another or alternative measure, the amount of the penetration enhancer(s) is sufficient to increase the bioavailability of the PPS in a unit dose of the composition comprising the PPS and the at least one coxib as described herein at least 5%, at least 10%, at least 20% or more usually, at least 30%, as may be determined from about 0.1 hour to about 3 hours after administration of the PPS, or more usually about 0.2 hours to about 0.6 hours, or about 0.3 hours to about 0.4 hours after administration of the PPS (e.g., at peak plasma concentration of the PPS).

Again, typically, a penetration enhancer, or combination of penetration enhancers, as described above acts to increase biological membrane penetration/permeation (e.g., of the gastrointestinal (GI) tract and generally, the lower GI tract) as distinct from increasing solubility of the PPS (e.g., in the PPS composition and/or in a mucous coating or layer of the biological membrane).

From the above, whilst in embodiments of the invention as described herein the PPS and the at least one coxib is administered in combination in the absence of a penetration enhancer, or combination of penetration enhancers, for increasing the oral bioavailability of PPS, in other embodiments, the PPS and the at least one coxib may be administered in combination with one or more excipients which whilst otherwise capable of acting to increase the oral bioavailability of PPS, are not present in the composition or administered, in an amount or dosage sufficient to increase the oral bioavailability of the PPS for therapeutically effective inhibition of the Lipoxygenase (LO) pathway of arachidonic acid (AA) metabolism as described herein.

Surprisingly, it has also been discovered by the inventors that encapsulating the PPS and coxib formulations as described herein in hydroxyl propyl methylcellulose (HPMC) capsule shells in place of the conventional gelatin capsules, together with excipients such as crystalline methylcellulose and magnesium stearate in place of the conventionally used lactose, improved the efficacy and tolerability of both the PPS containing composition embodied by the invention and the coxib that was used as the comparator control drug in the double blind clinical trial described herein (see Example 7 below).

By excluding lactose as an excipient in the capsules, it was reasoned it would reduce the potential risk of eliciting symptoms of lactose intolerance in not only the patients participating in the clinical trials, but also for a wider population who may utilise the preparation for the management of pain and/or inflammation in the future.

Lactose intolerance is a very common medical problem with up to 70% of the world's population being affected (Mill D, Dawson J, Johnson J L. Managing acute pain in patients who report lactose intolerance: the safety of an old excipient re-examined. Therapeutic Advances in Drug safety. 2018; 9: 227-235). Significantly, it was recognized by the instant inventors that currently available oral analgesics and NSAIDs used for the management of pain and inflammation, including celecoxibs, contain lactose as an excipient in their commercial formulations (Cook W, Me F, Rowe R, et al. (Eds). Pharmaceutical excipients, lactose monohydrate. London: Pharmaceutical Press, American Pharmacists Association, 2016, Mill D, Dawson J, Johnson J L. Managing acute pain in patients who report lactose intolerance: the safety of an old excipient re-examined. Therapeutic Advances in Drug safety. 2018; 9: 227-235). Further, as the regular use of NSAIDs, including coxibs, has been associated with the production of adverse gastrointestinal side effects (Lane L. Perspectives in pain management: Gastrointestinal effects of NSAIDs and Coxibs. J Pain and Symptom Management. 2003; 25:S32-S40, Mattia C, Colluzzi F. Cox-2 inhibitors: Pharmacological data and adverse side effects. Minerva Anestesiol. 2005; July-August(7-8):461-70), it was reasoned by the inventors that the gastrointestinal problems arising from lactose intolerance in such patients could be exacerbated by the daily consumption of lactose excipient in their medication.

Unexpectedly, the inventors have found not only that the combination of PPS and a coxib as described herein can provide improved alleviation of symptoms associated with different forms of OA but also, that pain symptoms may be better alleviated by the coxib alone when orally administered in a capsule formulation that did not contain lactose either as part of the capsule shell or as an excipient in the coxib formulation, though to a lesser degree in comparison to the combination of the PPS and coxib in the same lactose free capsule system.

Hence, there is further provided herein a pharmaceutical or veterinary composition comprising a therapeutically effective amount of at least one coxib and a therapeutically effective amount of pentosan polysulfate or a pharmaceutically acceptable salt thereof, wherein the composition does not contain lactose.

Still further, there is provided herein a pharmaceutical or veterinary composition comprising a therapeutically effective amount of at least one coxib together with a physiologically acceptable carrier or excipient(s), wherein the composition does not contain lactose.

As described herein, the lactose free composition may be in a solid dosage form (e.g., a powder, granules, a tablet) or other form such as a caplet or capsule.

Preferably also, compositions, capsules and capsule shell preparations used in composition preparations as described herein will be gelatin free. Excluding the use of animal (e.g., porcine) gelatin not only avoids any possible risk of potential transmission of BSE but also addresses any potential objections that may be raised against consumption of the capsules for religious or dietary reasons. Hydroxypropylmethyl cellulose (HPMC) capsules are preferred although in other embodiments, other suitable alternatives to gelatin containing shell or encapsulation systems can be employed.

Without being limited by theory, the inventors consider that the combination of PPS and coxibs as oral formulations act synergistically, not only in suppressing joint inflammation and pain via the COX and LOX enzyme systems, but also in providing prophylaxis for stoke, ischemia, atherosclerosis and deep vein thrombosis (DVT) in elderly patients with predispositions to these cardiovascular problems. Significantly, such thrombotic and cardiovascular problems are well documented serious adverse side effects associated with the use of coxibs, including celecoxib in patients with a predisposition to these diseases (Gislason G H, Jacobsen S, Rasmussen J N, Rasmussen S, Buch P, Friberg J, Schramm T K, Abildstrom S Z, Kober L, Madsen M, Torp-Pedersen C. Risk of death or re-infarction associated with the use of selective cyclooxygenase-2 inhibitors and nonselective nonsteroidal anti-inflammatory drugs after acute myocardial infarction Circulation. 2006; 113:2906-13, Brophy J M. Celecoxib and cardiovascular risks. Expert Opin. Drug Saf. 2005; 6:1005-15, Dajani E Z, Islam K. Cardiovascular and gastrointestinal toxicity of selective cyclooxygenase-2 inhibitors in man. J Physiol Pharmacol. 2008; 59Supp12: 117-33.

The prophylactic effects of Pentabrex™ formulations as described herein against the potential induction of stoke, ischemia, hypertension, or deep vein thrombosis (DVT) is proposed by the inventors to be due to the presence in the Pentabrex™ formulation of PPS. This is predicated on the knowledge that PPS has been demonstrated to ameliorate such circulatory and cardiovascular medical conditions when administered orally (Losonczy H, Nagy I, David M. Effects of various doses of SP4 on Fibrinolytic activity in patients with thrombotic disease. Folia Haematol., Liepzig. 1988; 115:388-393, Bobadilla N A, Tack I, Tapia E, et al. Pentosan polysulfate prevents glomerular hypertension and structural injury despite persisting hypertension in 5/6 nephrectomy rats. J Am Soc Nephrol. 2001; 12:2080-2087, Lupia E, Zheng F, Grosjean F, Tack I, Doublier S, Elliot S J, Vlassara H, Striker G E. Pentosan polysulfate inhibits atherosclerosis in Watanabe heritable hyperlipidemic rabbits: differential modulation of metalloproteinase-2 and -9. Lab Investigation. 2012; 92: 236-245). Furthermore, the present inventors propose that metabolic pathways implicated in the pathogenesis of cardiovascular disease, stroke, thrombosis and atherosclerosis could be abrogated by the synergistic action of PPS and celecoxib in the Pentabrex™ formulations.

Pentosan polysulfate is a polydisperse semi-synthetic sulfated polysaccharide (see structure shown in FIG. 1). The PPS used in compositions and methods in accordance with the invention will generally be unfractionated, although fractionated PPS preparations may also be employed, see e.g., United States Patent Publication No. 2011-0251154, the contents of which is incorporated herein in its entirety by cross-reference. Typically, the PPS has a weight average molecular weight (MW) range of from about 1,800 Da to about 17,000 Da, more preferably a weight average MW range of from about 4000 to 7000 Da and most preferably, a weight average MW of about 5700 Da. Typically, PPS useful in embodiments of the invention has a polydispersity of 2.0-2.4 and a sulfur content in a range of from 16% to 17% by weight. Preferably, PPS used in compositions and methods as described herein has a sulfur content of about 16% by weight. Preparations of PPS that can be utilised are, for example, commercially available from Bene-PharmaChem GmbH & Co KG, Bayerwaldstr, Geretsried, Germany.

Typically, a physiologically acceptable salt of PPS is employed. Suitable such salts that can be utilised besides the sodium salt (i.e., NaPPS) include the calcium (i.e., CaPPS) and magnesium (i.e., MgPPS) salts of PPS. NaPPS is particularly preferred.

A coxib and PPS composition embodied by the invention can be administered to the mammalian subject one or more times in a day to provide a total dosage of the coxib over the course of the day of up to about 800 mg that is, a total dosage of about e.g., 50 mg, 100 mg, 150 mg 200 mg, 250 mg, 300 mg, 350 mg, 400 mg, 450 mg, 500 mg, 550 mg, 600 mg, 650 mg, 700 mg, 750 mg or 800 mg. Generally, the total dosage of the coxib over a 24 hour period will be in a range of from about 100 mg up to about 600 mg and more usually, in a range of from about 250 mg to about 500 mg.

Typically, the dosage of the coxib per administration will be in the order of about 50 mg to about 300 mg, and more usually about 200 mg to about 250 mg.

The total dosage of the PPS over the 24 hour period will generally be up to about 1000 mg, e.g., a total dosage of about 50 mg, 100 mg, 150 mg 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg or about 1000 mg. Generally, the total dosage of the PPS will be in a range of from about 100 mg up to about 750 mg, more usually, in a range of about 150 mg to about 500 mg and most usually, about 250 mg to about 350 mg.

Typically, the dosage of the PPS per administration will be in the order of about 50 mg to about 300 mg, and more usually about 125-375 mg, or 175 mg to about 250 mg.

Most typically, the coxib and the PPS will be present in a composition embodied by the invention or administered to a mammalian subject in accordance with the invention in a ratio of about 1:1 to 1: 2 by weight. For example, when the coxib is celecoxib, a single daily dosage can comprise 125 mg celecoxib and 125 mg PPS, 175 mg celecoxib and 175 mg PPS or, e.g., 250 mg of celecoxib and 250 mg of the PPS administered 3-4 times weekly. However, other combinations of the coxib and PPS are provided for herein (e.g., 175 mg celecoxib and 125 mg PPS) and 175 mg celecoxib and 325 mg PPS (Pentabrex Forte™, Proteobioactives Pty Ltd, Balgowlah, NSW, Australia). All such therapeutically effective formulations of a coxib and PPS as described herein are expressly encompassed by the invention. Whilst the coxib and PPS can be administered on a daily basis, a treatment regimen in accordance with the invention will typically comprise administration of the coxib and the PPS one or more times a day or from 1 to 4 times a week.

The pain and/or inflammation that can be treated in accordance with the invention can be any pain and/or inflammation conventionally treated with a coxib or with PPS. Inflammation treatable in accordance with the invention for example will typically be characterized by overproduction of inflammatory mediators such as proinflammatory cytokines (e.g., IL-1, IFN-γ, IL-6, IL-12, IL-18, and granulocyte-macrophage colony stimulating factor (GM-CSF)). Examples of pain and inflammation that can be treated in embodiments of the invention include but are not limited to pain and/or inflammation arising from a rheumatic disease or condition, bone joint pain, bursitis, bone joint inflammation, bone marrow edema, synovial inflammation, synovitis, inflammation of tendons (tendonitis), gout, neck and lower back pain arising from e.g., degenerative changes in the vertebral discs and adjacent spinal structures (e.g., including lumbago and sciatica), spondylosis, ankylosing spondylitis, musculoskeletal diseases and conditions, and musculoskeletal pain e.g., including soft tissue trauma and sprains.

Rheumatic diseases and conditions that may be treated in accordance with the embodiments of the invention include, but are not limited to, arthritis, osteoarthritis, inflammatory arthritis, rheumatoid arthritis, idiopathic arthritis, juvenile rheumatoid arthritis, gout, gouty arthritis, pseudogout, and psoriatic arthritis.

The coxib and PPS can be provided in a pharmaceutical composition comprising a physiologically acceptable carrier suitable for oral administration to the intended subject. Typically, non-animal gelatin capsules such as HPMC capsules and excipients other than lactose are preferred.

A pharmaceutical or veterinary composition in accordance with the invention can, for example, be in the form of a solid such as ingestible granules or powder, tablet, caplet or pill. In other embodiments, the composition may be provided in the liquid form, for example, as a linctus, suspension, emulsion, syrup, troche, elixir, or other form suitable for oral administration such as powder or liquid filled capsules.

Pharmaceutical compositions useful in methods in accordance with the invention may include dispersion media and other excipients such as one or more of ethanol, polyols (e.g., glycerol, propylene glycol, liquid polyethylene glycol and the like), surfactants, vegetable oils and mixtures thereof.

A pharmaceutical composition as described herein can also incorporate one or more preservatives and other excipients suitable for oral administration such as may be selected from methyl, ethyl and propyl parabens, sodium benzoate, benzoic acid, potassium sorbate, propionic acid, sorbic acid, thimerosal, glycerol, and propylene glycerol. In addition, prolonged absorption of the composition may be brought about by use in the compositions of agents for delaying absorption such as aluminium monosterate and gelatin. Tablets, troches, pills, capsules and the like containing the coxib and PPS as described herein can also contain one or more of a binder such as gum tragacanth, acacia, corn starch or gelatin; a disintegrating agent such as corn starch, potato starch or alginic acid; a lubricant such as magnesium stearate; a sweetening agent such as sucrose, or saccharin; a flavouring agent; and diluent(s) amongst other excipient ingredients commonly used in pharmaceutical compositions for human or veterinary use. Whilst excipients other than lactose are preferred for reasons as described herein, the use of lactose is not excluded.

The use of ingredients and media as described above in pharmaceutical compositions is well known. Except insofar as any conventional media or ingredient is incompatible with the coxib or PPS as described herein, use thereof in prophylactic and therapeutic pharmaceutical compositions of the invention is included.

By use of the coxib and PPS "in combination" or in a "combination therapy" as used herein is meant simultaneous, separate or sequential administration of the coxib and the PPS in accordance in accordance with the invention in the same or different formulations whereby the coxib and the PPS exert their effect in over overlapping therapeutic windows.

In instances in which the coxib and PPS are administered sequentially, one will typically be administered essentially immediately after the other (e.g., within seconds or minutes) in order that they act together pharmacologically.

Typically, however, the coxib and the PPS are administered to the mammal simultaneously in the one composition. For veterinary uses, the coxib and PPS may be added to food and/or water for consumption by the animal.

It is particularly preferred to formulate a composition of the invention in dosage unit form for ease of administration and control over the uniformity of dosage to be used. Dosage unit form as used herein is to be taken to mean a physically discrete unit suited as a unitary dosage for the subject to be treated, each unit containing a respective predetermined quantity of each of the coxib and the PPS to produce the desired therapeutic or prophylactic effect. When the dosage unit form is, for example, a compressed capsule, tablet or pill, a coating (e.g., shellac, sugar, or enteric coating(s)) may be used to modify the physical form of the dosage unit to facilitate oral administration to the subject, and/or to e.g., obtain delayed release of the coxib and PPS.

A pharmaceutical composition embodied by the invention will generally contain at least about 1% by weight of each of the coxib and the PPS. The percentage may be varied and can conveniently be from about 5% to about 80% w/w or more of the preparation. Again, the amount of a coxib and the PPS in accordance with the invention will be such that an effective amount of each will be delivered to the subject.

The dosages of the coxib and PPS in accordance with the invention will depend on a number of factors including whether the coxib and PPS is to be administered for prophylactic or therapeutic use, the disorder, condition or purpose for which the agent is intended to be administered, the severity of the disorder or condition, the age of the subject, and related factors including weight and general health of the subject as may be determined by the physician, medical attendant or veterinarian in accordance with accepted principles. For instance, an initial dosage may initially be given which is subsequently increased or decreased at subsequent administrations following evaluation of the subject's response. Similarly, the frequency of administration may be determined in the same way that is, by continuously monitoring the subject's response between each dosage and if necessary, increasing the frequency of administration or alternatively, reducing the frequency of administration.

Typically, PPS will be administered in accordance with a method embodied by the invention to provide a dosage per administration of the PPS in a range of about 1 mg/kg body weight to about 4 mg/kg body weight of the subject. For a human, the dosage per administration will typically be about 2 mg/kg whilst for an animal such as a horse, dog or cat, the dosage may be higher.

The mammal treated as described herein may be any mammal treatable in accordance with the invention. For instance, the mammal may be a member of the equine (e.g., a horse), canine (e.g., a dog), feline (e.g., a house cat), bovine, porcine, ovine, rodent (e.g., a mouse, rat, guinea pig or hamster), Leporidae (e.g., a rabbit or hare) or primate (e.g. an ape, monkey, chimpanzee or baboon) animal families, or can be a human. Typically, when the mammal is a non-human animal, the mammal is selected from the group consisting of horses, and companion animals e.g., domestic dogs and cats).

When the mammal to be treated is a human the coxib will typically be celecoxib.

Coxibs that are used for the treatment of humans can of course also be administered to non-human mammals as described herein although the range of coxibs that may be employed for the treatment of non-human animals may be broader. Typically, celecoxib and meloxicam is also used in compositions and treatments of non-human animals as described herein. Celecoxib is widely available from commercial sources (e.g., see htttps://www.drugs.com).

Suitable pharmaceutically acceptable carriers and formulations useful in compositions of the present invention may for instance be found in handbooks and texts well known to the skilled addressee, such as "Remington: The Science and Practice of Pharmacy" 21st Edition, 2006 (Authors: J.P Remington and P. Beringer; Publisher: Lippincott Williams & Wilkins), the contents of which is incorporated herein in its entirety by cross-reference.

The invention will now be further described by reference to a number of non-limiting embodiments. The NaPPS ($M_w$=4000 Da to 7000 Da) utilised in the following examples was commercially obtained from Bene-PharmaChem GmbH & Co KG (Bene-PharmaChem GmbH & Co KG, Bayerwaldstr, Geretsried, Germany)

EXAMPLES

Example 1

JM: A fit and active 70-year-old female who had experienced symptoms of pain and joint stiffness in both hands and knees for 25 years. Radiological examination had confirmed some cartilage loss in peripheral joints as well as deterioration of disc space in cervical and lumbar spines. Physiotherapy and regular exercise (swimming and walking) and use of NSAIDs and paracetamol had provided some relief of the pain associated with the neck and lower back. However, these modalities failed to mitigate the pain in the peripheral joints, particularly in the hands. Hand-splints and combinations of higher doses of analgesics (codeine and paracetamol (Panadol™; GlaxoSmithKline Australia, Ermington, NSW, Australia) and twice daily Celebrex™ (200 mg) (Pfizer, Inc., USA) failed to provide lasting relief of pain and joint stiffness. Cortisone injections provided short-term relief but on the advice of her doctor they were terminated because of the known adverse side effects associated with the regular used of this class of drugs.

More recent radiological examination of JM's hands and knees showed increased joint space narrowing in the joints of the hands, particularly at the base of the thumb and the left knee. Pseudo gout was diagnosed and local cortisone injections were again initiated to the hand joints but the relief of pain was fleeting. Her hand specialist recommended surgery as the only treatment option remaining. The knee specialist recommended additional physiotherapy and maintenance of regular exercise. These regimens just maintained for approximately 12 months but the arthritic pain associated with use of her hands for daily activities were described as being excruciating.

JM then commenced a treatment protocol which required cessation of daily use of analgesics and Celebrex™ or any corticosteroids. These medications were substituted by thrice weekly oral administration of a formulation comprising 250 mg NaPPS (obtained from Bene-PharmaChem GmbH & Co KG, Germany, as described above) and 250 mg celecoxib (commercially available generic preparation) (Pentabrex™, a formulation of NaPPS and celecoxib embodied by the invention of Proteobioactives Pty Ltd, Balgowlah, NSW, Australia). Within 2-3 weeks of the commencement of this treatment JM reported that her joint pain, particularly of the hands had been substantially reduced, allowing her to undertake normal household and sporting activities. JM maintained this treatment regimen on an ongoing basis for 15 months with continued beneficial effects. She did not report any adverse side effects over this period.

Example 2

DA: A 74-year-old female diagnosed with idiopathic OA 5 years previously and prescribed 200 mg Celebrex™ daily with supplementation with analgesics such as paracetamol (Panadol™) when required by her doctor. The major sites of pain and stiffness were the ankles and hands but the pain emanating from these joints was not effectively attenuated by the Celebrex™ unless its daily use was supplemented with high doses of analgesics. DA discontinued use of analgesics and Celebrex™ and initiated oral use of only a formulation of comprising 250 mg NaPPS and 200 mg celecoxib (Pentabrex™; Proteobiactives Pty Ltd) thrice weekly, which she has continued to follow for 4 months. Within 2 weeks of commencing the new treatment protocol, DA reported a positive response and reported that she did not require the use of any analgesics to support the pain relief provided by the PPS and celecoxib formulation. During the subsequent 8 months DA changed her protocol to a daily oral dose to the 350 mg Pentabrex™ formulation (175 mg celecoxib and 175 mg NaPPS) with the same clinical outcomes without any accompanying adverse side effects.

Example 3

NW: An active 66-year-old female with joint pain arising from an early traumatic injury to the left knee that resulted in a torn medial meniscus and medial compartment loss of articular cartilage. NW also experienced moderate pain from the posterior compartment of her right knee that was diagnosed as arising from bursitis. These symptoms were partially managed over a number of years with the use of a variety of NSAIDs. Within the previous 2 years NW was prescribed Celebrex™. However, the pain and joint stiffness were not satisfactorily resolved by this drug and symptoms were exacerbated by exercises such as heavy gardening, walking and playing golf NW commenced treatment with a formulation comprising two 250 mg Pentabrex™ HPMC capsules each containing (125 mg Celebrex and 125 mg NaPPS) taken orally thrice weekly, and reported therapeutic benefits with respect to amelioration of joint pain, improved joint function and wellbeing after 2-3 weeks of commencing this treatment protocol. NW maintained this regimen on an ongoing basis for a further 12 months. The protocol was then changed to oral daily dose of a single 250 mg Pentabrex™ (containing 125 mg Celebrex and 125 mg NaPPS). Using this new regimen symptomatic relief was maintained as before. During the period of these treatments NW did not observe any adverse side effects while using the daily 250 mg Pentabrex™ formulation or thrice weekly 500 mg Pentabrex™ formulation.

Example 4

PG: An active 77 year old male with a history of sport induced post-traumatic osteoarthritis (PTOA) exacerbated by mild bilateral genu valgum leading to medial compartment cartilage loss and bone edema. PG had been a regular user of complementary medicines of putative therapeutic benefits together with regular use of Celebrex™. However, the symptoms of joint pain exacerbated by physical activity remained unresolved and he commenced treatment with a Pentabrex™ formulation comprising 250 mg NaPPS and 250 mg celecoxib (500 mg Pentabrex™, Proteobiactives Pty Ltd) taken orally on an ongoing thrice weekly basis. PG reported amelioration of arthritic symptoms, and reduction in daily use of hypertension medications while maintaining acceptable blood pressure. During the subsequent 12 months PG changed his protocol to a daily oral dose of the 350 mg Pentabrex™ formulation (containing 175 mg Celecoxib and 175 mg NaPPS). This formulation provided the same positive clinical outcomes as initially experienced, again without any accompanying adverse side effects.

Example 5

LM: A generally fit 72 year old male experienced unacceptable pain at rest from his left hip joint that was exacerbated on walking. Radiological examination showed almost complete loss of joint articular cartilage corresponding to Kellgren and Lawrence grade 4 OA. Following hip replacement surgery and subsequent physiotherapy the pain was resolved. However, within 6 months of the operation he complained of pain arising from his contralateral hip joint and lumbar spine. Subsequent radiographic examination of his spine revealed loss of disc height and marginal osteophytes indicative of spinal OA. This pain was not ameliorated by oral analgesics or NSAIDs including daily consumption of Celebrex™ (200 mg).

LM was then treated with Pentabrex™ composed of 250 mg NaPPS and 200 mg celecoxib (Proteobiactives Pty Ltd) taken orally thrice weekly. After following this regimen for 6-12 weeks LM reported total relief of pain emanating from both his right hip joint and lumbar spine. No adverse side effects attributable to the medications were reported by LM over this period.

Example 6

In this study, five female patients with established OA of the hands were enlisted in an open clinical trial to evaluate the efficacy and tolerability of a Pentabrex™ formulation (2×250 mg capsules, each capsule containing 125 mg Celecoxib and 125 mg NaPPS) when taken orally 3 times a week for 6 weeks. These patients were referred to the Subiaco Rheumatology Clinic (Subiaco, Perth, WA, Australia) as their OA symptoms were not satisfactorily resolved by their current usage of analgesics or NSAIDs (including coxibs). To be included in the clinical trial, patients had to be 50 years of age or older and have an OA grade of 3-4 (Kellgren J H, Lawrence J S. Radiological assessment of osteoarthrosis. Annals Rheumatic Dis.1957; 16:494-502) that had been symptomatic for at least 6 months Following their consent to participate in the study, patient's details of the symptomatic hand joints affected and grade of OA were recorded and the level of hand pain and stiffness determined to provide baseline values using validated 10 cm visual analogue scale (VAS) scoring systems (Sokka T. Assessment of pain in patients with rheumatic diseases. Best Pract Res Clin Rheumatol, 2003; 17:427-49, Domenica A. Delgado, D A, Lambert B, Boutris N, McCulloch P C, Robbins A B, Moreno M R, Harris J D. Validation of Digital Visual Analog Scale Pain Scoring with a Traditional Paper-based Visual Analog Scale in Adults. JAAOS Glob Res Rev 2018; 2:e088 DOI:10.5434/). The duration of their early morning hand stiffness was recorded in minutes, and the grip strength of the symptomatic hand quantified (in kgs) using a Constant electronic hand dynamometer (model number 14192-709E). The use of a dynamometer to quantify grip strength in patients with hand OA has also been validated (Villafañe J H, Valdes K, Vanti C, Pillastrini P, Borboni A. Reliability of handgrip strength test in elderly subjects with unilateral thumb carpometacarpal osteoarthritis HAND. 2015; 10:205-209. DOI 10.1007/s11552-014-9678-y). The patients were then provided with six week supplies of Pentabrex™ contained in labelled containers. Over the 6 week study period, patients were requested to refrain from using additional analgesics or NSAIDs unless absolutely necessary and return the container provide for the Pentabrex™ formulation to confirm compliance.

The 4 patients who completed the six week study were re-examined to determine the final values of the same medical parameters that were assessed at the commencement of the study. The net changes between the baseline values and the corresponding final values were calculated and the % change from baseline for each parameter determined. Patient's blood was also collected for routine haematological analysis plus additional assessment of Activated Partial thromboplastin time (APTT) and Prothrombin times (PT) at the time of commencement of the trial and immediately after its completion.

Table 1 summarises the results of the study. Apart from patient #2, who dropped-out only after one week stating that the medication was not affective, all of the remaining patients who completed the six week trial reported positive outcomes with no adverse side effects. The mean percentage changes from baseline of hand OA symptoms of pain (−58.9%), grip strength (+32.68%), joint stiffness (−45.55%) and duration of stiffness (−29.16%) for the group confirmed the overall significant improvement in the symptoms of hand OA without supplementary use of commercially available non-opioid analgesiscs or NSAIDs. Examination of the blood samples determined at the commencement and termination of the study showed no abnormalities in their haematological parameters.

TABLE 1

Pentabrex ™ Hand OA open clinical study

| Patient details and protocol followed: Pentabrex ® (500 mg) HPMC capsules each bulked with crystalline methyl cellulose and magnesium stearate taken orally 3 × weekly for 6 weeks. Assessed clinically before (Baseline values) and after study completed (Final values). | | | Hand Joint Pain (VAS 0-10 cm) | Hand-Grip Strength (Kg) | Hand Stiffness (VAS 0-10 cm) | Duration of Joint Stiffness (Minutes) |
|---|---|---|---|---|---|---|
| Female #1 age 67 Joints affected: 3 PIPs Osteophytes 3 & 5 PIPs, Grade 3 OA | | | | | | |
| Blood taken | yes | Baseline values | 5.0 | 12.6 | 7.5 | 60 |

TABLE 1-continued

Pentabrex ™ Hand OA open clinical study

Patient details and protocol followed: Pentabrex ® (500 mg) HPMC capsules each bulked with crystalline methyl cellulose and magnesium stearate taken orally 3 × weekly for 6 weeks. Assessed clinically before (Baseline values) and after study completed (Final values).

| | | | Hand Joint Pain (VAS 0-10 cm) | Hand-Grip Strength (Kg) | Hand Stiffness (VAS 0-10 cm) | Duration of Joint Stiffness (Minutes) |
|---|---|---|---|---|---|---|
| Blood taken | yes | Final values | 3.5 | 14.5 | 2.5 | 30 |
| Results | No change | Net Change | −1.5 | +1.9 | −5.0 | −30 |
| | | % Change from baseline | −30% | +15% | −66.66% | −50% |

Female #2: Only completed 1 week of medication therefore excluded.
Female #3 aged 71
Grade 3.OA both hands

| | | | | | | |
|---|---|---|---|---|---|---|
| Blood taken | yes | Baseline values | 5.5 | 18.0 | 5.0 | 30 |
| Blood taken | yes | Final values | 4.0 | 24.9 | 3.0 | 10 |
| Results | No change | Net Change | −1.5 | +6.9 | −2.0 | −20 |
| | | % Change from baseline | −27.27% | +38.33% | −40% | −66.66% |

Female #4 aged 56
$4^{th}$ PIP & all DIPs both hands, Grade 3 OA

| | | | | | | |
|---|---|---|---|---|---|---|
| Blood taken | yes | Baseline values | 4.8 | Not done | 6.0 | 30 |
| Blood taken | yes | Final values | 0.2 | Not done | 1.0 | 5.0 |
| Results | No change | Net Change | −4.6 | | −5.0 | −25 |
| | | % Change from baseline | −95.83% | — | −83.33% | −83.33% |

Female #5 aged 56
DIPs & $2^{nd}$ MCP confirmed by x-rays

| | | | | | | |
|---|---|---|---|---|---|---|
| Blood taken | yes | Baseline values | 5.8 | 32.2 | 7.2 | 30 |
| Bloods taken | yes | Final values | 1.0 | 46.6 | 2.0 | 15 |
| Results | No change | Net Change | −4.8 | +14.4 | −5.2 | 15 |
| | | % Change from Baseline | −82.75% | +44.72 | −72.22 | −50% |
| Mean values change (%) | | | −58.9 | +32.68 | −45.55 | −29.16 |

Example 7

A prospective, dose ranging, double-blind, comparator clinical trial to evaluate the tolerability and efficacy of Pentabrex™, (Proteobioactives Pty Ltd, Balgowlah, NSW, Australia) compared to celecoxib, for the relief of symptoms in elderly patients with OA of the hand and knee conducted at the Subiaco Rheumatology Clinic, Subiaco, Perth, WA, Australia.

1. Patient Inclusion and Exclusion Criteria

Thirty three male and female patients with symptomatic hand or knee OA were obtained from referrals sent by general medical practitioners located in Perth (Western Australia) suburbs. These patients were referred to the Subiaco Rheumatology Clinic as their OA symptoms were not satisfactorily resolved by their current usage of analgesics or NSAIDs (including coxibs). To be included in the clinical trial, patients had to be 50 years of age or older and have an OA grade of 3-4 (Kellgren J H, Lawrence J S. Radiological assessment of osteoarthrosis. Annals Rheumatic Dis.1957; 16:494-502) that had been symptomatic for at least 6 months prior to their inclusion. If a patient had pain in both knees or both hands, the more painful knee or hand was the joint used for assessment. If patients had both hand and knee OA each most painful joint was assessed separately.

Patients with rheumatoid arthritis or any other rheumatic condition that required the continuous administration of a second line rheumatic agent such as methotrexate, steroid or cytokine antagonist, had current bleeding diathesis or were receiving treatment with blood thinners (such as warfarin), or had any significant medical conditions involving the liver, kidney, or their motor or nervous systems were excluded from the trial.

Although patients were requested not to consume additional analgesics or NSAIDs over the duration of the study, if they found this to be too difficult because of the unacceptable level of pain they experienced, they were required to document the drugs and quantities they used for relief of pain in a six week daily diary that supplied with the clinical trial test package manufactured by the compounding chemist (Kingsway, Brookvale NSW 2100, Australia). Failure to complete the daily dairies over the duration of the 6 week trial and return the used blister pack to the examining clinician at the final consultation would be taken as to non-compliance with the trial protocol. The diary requirement was included as part of patient assessment for the duration of the trial because of the known non-compliance of patients taking oral medications over extended periods of time (van Berge Henegouwen MTH, van Driel H F, Kasteleijn-Nolst DGA. A patient diary as a tool to improve medicine compliance. Pharm World Sci. 1999; 21: 21-24, Farmer K C, Methods for measuring and monitoring medication regimen adherence in clinical trials and clinical practice. Clinical Therapeutics. 1999; 21:1074-1090).

This study was conducted in accordance with the principles of the Declaration of Helsinki for undertaking medical research on human subjects. All the eligible patients recruited for the trial provided written informed consent to participate.

2. Dosages Regimens for Double Blind Comparator Clinical Study

Two test dosage formulations of Pentabrex™ were examined in this study as follows.
  (a) Pentabrex™ (350 mg) HPMC capsules containing PPS (175 mg) and celecoxib (175 mg) together with crystalline methyl cellulose and magnesium stearate as the only excipients. Patients were requested to take a single capsule with water daily for 6 weeks from the blister pack supplied.
  (b) Pentabrex Forte™: HPMC capsules containing PPS (325 mg) and celecoxib (175 mg) together with crystalline methyl cellulose and magnesium stearate as the only excipients. Patients were requested to take a single capsule with water daily for 6 weeks. Pentabrex™ (Pentacoxib™) and Pentabrex Forte™ are trade mark of Proteobioactives Pty Ltd, Balgowlah, NSW, Australia.

HPMC capsules containing celecoxib (175 mg) together with crystalline methyl cellulose and magnesium stearate as the only excipients were used as the celecoxib comparator control drug for comparison with both Pentabrex™ and Pentabrex Forte™ formulations. Patients taking control capsules were again requested to take a single capsule with water daily for 6 weeks from the blister pack supplied.

The PPS utilised in this study is a pharmaceutical product manufactured by Bene-PharmaChem GmbH & Co, Geretscied, Germany. The celecoxib was provided by Kingsway Compounding Chemists, Brookvale, NSW, Australia. All materials used in the formulations were of documented USP grade and approved for human oral application by the Therapeutic Goods Administration (TGA), Canberra, ACT, Australia.

3. Methods of Assessment

At the commencement of the trial details of the patient's age, height, weight, location of the most painful joints, duration of symptoms and grade of OA were recorded. For patients with hand OA the level of pain and stiffness determined using a validated 10 cm visual analogue scale (VAS) scoring systems (Sokka T. Assessment of pain in patients with rheumatic diseases. Best Pract Res Clin Rheumatol, 2003; 17:427-49, Domenica A. Delgado, D A, Lambert B, Boutris N, McCulloch P C, Robbins A B, Moreno M R, Harris J D. Validation of Digital Visual Analog Scale Pain Scoring with a Traditional Paper-based Visual Analog Scale in Adults. JAAOS Glob Res Rev 2018; 2:e088 DOI: 10.5434/). The duration of their early morning hand stiffness was recorded in minutes, and grip strength of their symptomatic hand quantified (in kgs) using a Constant electronic hand dynamometer (model number 14192-709E). The use of dynamometer to quantify grip strength in patients with hand OA has also been validated (Villafañe J H, Valdes K, Vanti C, Pillastrini P, Borboni A. Reliability of handgrip strength test in elderly subjects with unilateral thumb carpometacarpal osteoarthritis HAND. 2015; 10:205-209. DOI 10.1007/s11552-014-9678-y).

For patients with OA of the knee joints their VAS pain scores were determined for their pain at rest, pain on walking and early morning stiffness. The duration of knee joint stiffness was recorded in minutes and global pain was assessed on a 5-point scale corresponding to 0=no pain, 1=slight pain, 2=mild pain, 3=moderate pain and 4=severe pain.

The same clinical parameters that were determined for all patients at baseline were assessed at the final examination six weeks later. The patient's diaries and blister packs returned were also examined and the number of supplementary analgesics they consumed was recorded. Any adverse side effects noted over the duration of the trial were also recorded. Patient's blood was collected for routine haematological analysis plus additional assessment of Activated Partial thromboplastin time (APTT) and Prothrombin times (PT) at the tune of commenced of the trial and immediately after its completion.

4. Results and Discussion

Analysis of the demographics of all the patients who completed the six week duration of the double blinded Pentabrex™ clinical trial are shown in Table 2. Two tailed Student's T-Test analysis of the two populations used for the clinical trial showed that they were not statistically different.

TABLE 2

Patient demographics

| Patient ID | Sex | Age | BMI | Joint site | KL grade | Duration |
|---|---|---|---|---|---|---|
| Pentabrex ™ Group | | | | | | |
| Patient #1 | F | 72 | 27.4 | Hand | 3 | 8 |
| Patient #4 | F | 65 | — | Hand | 3 | 12 |
| Patient #5 | F | 67 | 27.4 | Hand | 3 | 1 |
| Patient #11 | M | 75 | 29.1 | Hand | 3 | 4 |
| Patient #14 | M | 70 | 32.6 | knee | 3 | 5 |
| Patient #17 | M | 59 | 28.4 | hand | 3 | 5 |
| Patient #18 | M | 55 | 42.4 | knee | 3 | 3 |
| Patient #19 | F | 58 | 40 | knee | 3 | 15 |
| Patient #24 | F | 80 | 34 | knee | 4 | 1 |
| Patient #29 | F | 72 | 34.4 | knee | 3 | 5 |
| Means | | 67.3 | 32.85 | | 3 | 5.9 |
| Celecoxib Group | | | | | | |
| Patient #2 | F | 55 | 33.2 | knee | 3 | 8 |
| Patient #3 | F | 69 | 28.3 | knee | 3 | 1 |
| Patient #6 | F | 57 | 40.4 | knee | 3 | 4 |
| Patient #7 | F | 57 | 30.1 | knee | 3 | —* |
| Patient #12 | M | 64 | 33.2 | hand | 3 | 15 |
| Patient #13 | F | 70 | 32 | knee | 3 | 5 |
| Patient #15 | F | 73 | 22.2 | knee | 3 | 0.5 |

TABLE 2-continued

Patient demographics

| Patient ID | Sex | Age | BMI | Joint site | KL grade | Duration |
|---|---|---|---|---|---|---|
| Patient #15 | F | 73 | 22.2 | hand | 3 | 0.5 |
| Patient #20 | F | 77 | 27.3 | knee | 3 | 15 |
| Patient #21 | F | 53 | 28.1 | hand | 3 | 4 |
| Patient #22 | F | 66 | 30.5 | knee | 3 | 1 |
| Patient #26 | F | 78 | 24.4 | hand | 3 | 8 |
| Patient #27 | F | 60 | 24.9 | knee | —* | 3 |
| Means | | 65.54 | 29 | | 3 | 5.41 |
| T-Test between groups | | $p < 0.62$ | $p < 0.1$ | | $p < 0.28$ | $p < 0.82$ |

Three patients from the Pentabrex ™ group (#8, #9, 23) and two from the Celecoxib Group (#10 and #16) were excluded due to non-compliance with trial protocol.
*Data not recorded The means and standard deviation of the mean of the percentage change from baseline scores calculated for the all the individual patients with hand OA who completed the are shown graphically in FIG. 3.

Apart from the % change in VAS pain scores, the duration of joint stiffness and grip strength, determined before and after completion of the comparator trial for hand OA patients, the number of analgesics they consumed was also included. Any values that fell below 0.0% indicated that the patients' symptoms were worse after completing the trial.

Although analysis of these data by two-way analysis of variance (ANOVA) using Graphpad Prism 7.0d software (La Jolla, California, USA) failed to demonstrate statistically significance differences between the two test treatment groups, the mean values for the individual patient's clinical parameters determined for the Pentbrex™ group were generally higher than for the corresponding celecoxib control group, suggesting a more consistent response to treatment.

A similar response to the two treatments was observed for the patients with Knee OA, the results of which are shown in FIG. 4. However, with this group it was evident that patients in the celecoxib control group consumed a larger number of supplementary analgesics over the course of the trial. The additional analgesic effects possible mediated by use of these supplementary drugs might have contribute to pain relief in this group.

Routine laboratory hematological analysis, plus additional clotting parameters, determined from the patient's blood samples collected before and after completion of the clinical trial failed to show any abnormal variations in values.

Only three patients (one hand OA +two knee OA) were enrolled and completed the Pentabrex Forte™ group double blinded study which prohibited statistical comparison with the 175 mg celecoxib control groups. The individual results for these three Pentabrex Forte™ treated patients are therefore documented in Tables 3A, 3B, 3C. One of these patients (#31) was a female with hand OA who obtained a positive respond to the Pentabrex Forte™ formulation and did not required any additional analgesic or anti-inflammatory supplementary drugs over the 6 week study (see Table 3A). Two patients (#34 and #35) were both male who presented with OA of the knee joints. Both these male patients also reported a very positive response to the Pentabrex Forte™ formulation and again did not require any supplementary analgesic or anti-inflammatory medications over the course of the study (see Tables 3B and 3C).

TABLE 3A

Results for Patient #31 who completed the Pentabrex Forte ™* six week hand
OA double blinded comparator clinical trial
Patient Name: JF Patient number: 31 Sex: Female Age: 62
Weight: 78 kg Height: 165 cm Hand Joints affected: Left DIP and PIP joints
Duration of disease: 5 years OA X-Ray Score: Moderate (K&L grade 3)
Date of commencement: Nov. 30, 2018 Date of completion: Jan. 12, 2019
Number of analgesics or other NSAIDS taken during study: NIL

| Bloods taken start: Yes Bloods taken Finish: Yes# | VAS Pain (0-10 cm) | Hand Grip Strength (Kg) | VAS Pain— Morning Stiffness (0-10 cm) | Stiffness pain Duration (mins) |
|---|---|---|---|---|
| Baseline values | 5.8 | 15.5 | 6.0 | 30 |
| Final values | 4.0 | 22.3 | 4.0 | 10 |
| Net Change | 1.8 | 6.8 | 2.0 | 20 |
| % Change from baseline | 68.9 | 30.5 | 33.33 | 66.66 |

*Pentabrex Forte ™ = 325 mg PPS + 175 mg celecoxib in a single HPMC capsule
Hematological analysis of blood samples showed no deviation in parameters from normal values

TABLE 3B

Results for Patient #34 who completed the Pentabrex Forte ™* six week knee
OA double blinded comparator clinical trial
Patient Name NS Patient number: 34 Sex: Male Age: 50
Weight: 80 kg Height: 170 cm Joints affected: Right Knee
Duration of symptoms: 2 years OA X-Ray Score: Moderate (K&L grade 3)
Date of commencement of treatment: Dec. 3, 2018 Date of completion: Jan. 16, 2019
Number of analgesics or other NSAIDS taken during study: NIL

| | BASELINE VALUES | FINAL VALUES | CHANGE FROM BASELINE | % CHANGE FROM BASELINE |
|---|---|---|---|---|
| VAS knee rest pain (0-10 cm) | 0.0 | 0.0 | 0.0 | 0.0 |
| VAS knee walk pain (0-10 cm) | 7.2 | 3.5 | 3.7 | 51.38 |
| VAS morning stiffness pain (EMS) (0-10 cm) | 5.5 | 0.5 | 5.0 | 90.9 |
| Duration of EMS (Mins) | 5.0 | 1.0 | 4.0 | 80.0 |
| Joint range of motion (degrees) | Full | Full | 0.0 | |
| Bloods taken for biochemistry & hematology + APTT test | Yes | Yes# | | |
| Global Pain score: 0 = None, 1 = Slight, 2 = Mild, 3 = Moderate, 4 = Severe | 3 | 1 | 2 | 33.33 |

*Pentabrex Forte ™ = 325 mg PPS + 175 mg celecoxib in a single HPMC capsule
Hematological analysis of blood samples showed no deviation in parameters from normal values

TABLE 3C

Results for Patient #35 who completed the Pentabrex Forte ™* six week knee
OA double blinded comparator clinical trial
Patient Name J S-S Patient number: 35 Sex: Male Age: 51
Weight: 104 kg Height: 185 cm Joints affected: Left Knee
Duration of symptoms: 5 years OA X-Ray Score: Moderate-severe (K&L grade 3-4)
Date of commencement of treatment: Dec. 17, 2018 Date of completion: Jan. 29, 2019
Number of analgesics or other NSAIDS taken during study: NIL

|  | BASELINE VALUES | FINAL VALUES | CHANGE FROM BASELINE | % CHANGE FROM BASELINE |
|---|---|---|---|---|
| VAS knee rest pain (0-10 cm) | 2.0 | 0.0 | 2.0 | 100.0 |
| VAS knee walk pain (0-10 cm) | 5.5 | 0.5 | 5.0 | 90.9 |
| VAS morning stiffness pain (EMS) (0-10 cm) | 5.8 | 0.5 | 5.3 | 91.4 |
| Duration of EMS (Mins) | 10.0 | 0.5 | 9.5 | 95.0 |
| Joint range of motion (degrees) | 180-120 | 180-160 | 40° | 22.22 |
| Bloods taken for biochemistry & hematology + APTT test | Yes | Yes# |  |  |
| Global Pain score: 0 = None, 1 = Slight, 2 = Mild, 3 = Moderate, 4 = Severe | 3 | 0 | 3 | 100 |

*Pentabrex Forte ™ = 325 mg PPS + 175 mg celecoxib in a single HPMC capsule
Hematological analysis of blood samples showed no deviation in parameters from normal values Review of the open clinical studies (Examples 1-6) described above which included patients with symptoms arising from osteoarthritis of their hand, knee and spine (disc) joints all showed a positive response to the Pentabrex™ oral formulations. However, individuals with hand OA responded particularly well to the Pentabrex™ medication which prompted a separate controlled open clinical study conducted with only female patients with hand OA (Example 6). This study confirmed the efficacy and tolerability of Pentabrex™ for providing symptomatic relief in patients with hand OA.

The results generated by the present studies indicate that encapsulating the PPS and coxib medications in non-gelatin capsules without the inclusion of lactose as an excipient was beneficial in terms of efficacy and tolerability for both Pentabrex™ and celecoxib. The reported widespread incidence of lactose intolerance in the general population leads the inventors to suggest that elimination of this particular saccharide from formulations used in the study was a possible contributing factor, particularly for the elderly OA patients recruited for our clinical studies who generally had a prior history of long-term consumption of NSAIDs (including celecoxibs) and OTC analgesics which have well documented gastrointestinal adverse effects associated with chronic usage.

Apart from the aforementioned safety, dietary, and religious advantages of replacing the use of gelatin capsules for Pentabrex™ formulations with HPMC shells, this modification may have altered the dissolution and pharmokinetics of the Pentabrex™ PPS and celecoxib active components as it is known that HPMC capsules have different dissolution kinetics than hard gelatin capsule shells. In addition, it has recently been shown that sulfated polysaccharides such as carrageenan form quite stable complexes with gelatin due to ionic and other molecular interactions between various sites within these two polymers (Voron'ko N G, Derkach S R, Vovk M A, Tolstoy P M. Complexation of Carrageenan with gelatin in aqueous phase analysed by $^1$H NMR kinetics and relaxation. Carbohydrate Polymers. 2017; 169:117-126). It is possible therefore that the highly negatively PPS molecules of Pentabrex™ could bind to the positively charged ε-aminoacids located along the gelatin polypeptide sequence. Such molecular interactions could influence the rate of dissolution of PPS from the gelatin capsules and thus its eventual concentration and within the gastrointestinal tract. In contrast, HPMC does not contain any cationic amino acids or other positively charges molecular sites within it's structure that could bind PPS and therefore would be predicted not to significant influence PPS dissolution and thus rate of absorption when administered orally. However, comparative dissolution and pharmacokinetic studies with the Pentabrex™ formulations using HPMC and gelatin hard shell capsules are required to confirm this explanation.

Although the outcome of the statistical analysis of results obtained for all the patients with hand and knee OA who participated in the prospective double blind comparator clinical trial failed to reach significance, the means values obtained for their individual percentage change from baseline scores were generally higher than the corresponding scores for the celecoxib treated group (FIGS. 3 and 4). However, the overall responses to Pentabrex™ observed for the hand OA group appeared to be more consistent than for the knee OA group.

In order to pursue this observation further, the inventors divided all the overall clinical outcomes obtained for the patients who completed the double blind clinical trial using the daily Pentabrex™ (350 mg) dose into two groups—positive responders and negative (nil) responders. The results of this analysis are shown below in Table 4.

TABLE 4

Summary of patient overall response to test medications used in the double blind active comparator clinical trial

| | Pentabrex™ Group | | | Celecoxib Group | |
|---|---|---|---|---|---|
| Patient—ID | Positive response | Negative response | Patient—ID | Positive response | Negative response |
| Hand OA | | | Hand OA | | |
| Patient #1 | X | | Patient #12 | | X |
| Patient #4 | X | | Patient #15* | | X |
| Patiemt #5 | X | | Patient #21 | X | |
| Patient #11 | X | | Patient #26 | | X |
| Patient #17 | | X | | | |
| n = 5 | 4 | 1 | n = 4 | 1 | 3 |
| % | 80 | 20 | % | 25 | 75 |
| Knee OA | | | Knee OA | | |
| Patient #14 | X | | Patient #2 | X | |
| Patient #18 | X | | Patient #3 | X | |
| Patient #19 | X | | Patient #6 | X | |
| Patient #24 | X | | Patient #7 | X | |
| Patient #29 | | X | Patient #13 | | X |
| | | | Patient #15* | | X |
| | | | Patient #20 | X | |
| | | | Patient #22 | X | |
| | | | Patient #27 | X | |
| n = 5 | 4 | 1 | n = 9 | 7 | 2 |
| % | 80 | 20 | % | 77.77 | 23.33 |
| Combined patient Hand and Knee OA overall responses to test medication | | | | | |
| n = | 8 | 2 | n = | 8 | 5 |
| % | 80 | 20 | % | 61.54 | 38.46 |

*Patient # 15 evaluated for both hands and knees

As is evident from Table 4, the analysis revealed that the overall patient group response to the Pentabrex™ formulation for both the hand (80%) and knee OA (80%) groups was more positive than for the corresponding celecoxib treated group of 25% and 77.77% respectively. In addition, the analysis showed that the percentage of the hand OA patients who benefited from the Pentabrex™ medication was substantially higher than for the corresponding celecoxib treated control group, while the knee OA group treated controls were less effective. The limited number of patients recruited for the Pentabrex Forte™ dose double blind study prohibited a similar analysis to the above to be performed. However, all three patients who completed the trial reported a positive improvement of their clinical symptoms using this formulation.

Osteoarthritis of the hand is highly prevalent in elderly populations of developed countries. For example, in the USA more than 50% of 60-year-old individuals show radiographic evidence of hand OA (Altman R D. Pharmacological therapies for osteoarthritis of the hand: a review of the evidence. Drugs Aging. 2010; 27:729-45), while in Japan the prevalence of hand OA with KL grade ≥2 has been reported to be as high as 89.9% in elderly males and 92.3% in females (Kodama R, Muraki S, Oka H, Iidaka et al. Prevalence of hand osteoarthritis and its relationship to hand pain and grip strength in Japan: The third survey of the ROAD study. Mod Rheumatol. 2016; 26:767-73).

Hand OA has been considered to be a more erosive disease than hip and knee OA and is still treated with traditional analgesics and NSAIDs but with limited success. However, hand OA has now been shown to respond more favorably to more powerful anti-arthritic drugs such as methotrexate (Haugan I K. Hand osteoarthritis: Current Knowledge and new ideas. Scand J Rheumatology. 2016; 45(sup128): 58 63, Pavelka K, Olejarova M, Pavelkova A. Methotrexate in the treatment of erosive OA of the hands. Ann Rheum Dis. 2006; 65[Suppl 11]:402) which supports the concept that hand OA is more an inflammatory disease.

More recently European research groups have employed longitudinal magnetic resonance imaging (MRI) studies to investigate in more detail the underlying pathology of hand OA (Haugan I K. Hand osteoarthritis: Current Knowledge and new ideas. Scand J Rheumatology. 2016; 45(sup128): 58 63, Haugen I K, Slatkowsky Christensen B, Boyesen P, Sesseng S, van der Heijde D, Kvien T K. Increasing synovitis and bone marrow lesions are associated with incident joint tenderness in hand osteoarthritis. Ann Rheum Dis. 2016; 75:702-8, Liu R, W. Damman W, Reijnierse M, J. L. Bloem J L, Rosendaal F R, Kloppenburg M. Bone marrow lesions on magnetic resonance imaging in hand osteoarthritis are associated with pain and interact with synovitis. Osteoarthritis and Cartilage. 2017; 25: 1093-1099).

These recently published reports of the high incidence of bone marrow lesions (BML) in joints of patients with symptomatic hand OA could provide a possible explanation for the favorable clinical outcomes observed in the present clinical studies since a previous report (Ghosh P. Patent CA2826166A1-Treatment of bone marrow edema (oedema) (BME)) with polysulfated polysaccharides. Publication date Aug. 9, 2012) had shown that PPS when administered systemically (IM or SC) resolved the bone marrow lesions (oedema) and accompanying pain in patients diagnosed with this bone marrow pathology by MRI. It should be noted in this context that BME is synonymous with BML (Eriksen E F, Treatment of bone marrow lesions (bone marrow edema). Bone KEy Reports. 2015; doi:10.1038/bonekey.2015.124).

As such, it is proposed by the inventors that in one or more embodiments, the combination of PPS and celecoxib as in the Pentabrex™ and the Pentabrex™ Forte preparations described herein may be used as an oral drug for resolving the lesions of BME and the symptoms that can arise from this joint pathology by virtue of the aformentioned synergistic interactions between PPS and celecoxib.

Although a number of embodiments of the invention have been described above it will be understood that various modifications and changes may be made thereto without departing from the invention. The above described embodiments are therefore only illustrative and are not to be taken as being restrictive.

The invention claimed is:

1. A pharmaceutical or veterinary composition for oral administration comprising a therapeutically effective amount of at least one coxib and a therapeutically effective amount of unfractionated sodium pentosan polysulfate contained in a hydroxy propyl methylcellulose capsule, with the proviso that the composition does not include a penetration enhancer for increasing bioavailability of the unfractionated sodium pentosan polysulfate.

2. The composition according to claim 1, wherein the coxib is selected from the group consisting of celecoxib, rofecoxib, valdecoxib, parecoxib, etoricoxib, lumiracoxib, and firocoxib.

3. The composition for according to claim 2, wherein the composition comprises celecoxib.

4. The composition according to claim 1, wherein the unfractionated sodium pentosan polysulfate has a weight average molecular weight in a range of from about 1800 Da to about 17000 Da and a polydispersity of from about 2.0 to about 2.4.

5. The composition according to claim 1, wherein the composition comprises up to about 400 mg of the unfractionated sodium pentosan polysulfate.

6. The composition according to claim 1, wherein the composition comprises the unfractionated sodium pentosan polysulfate in an amount of from about 125 mg to about 375 mg.

7. The composition according to claim 6, comprising from about 50 mg to about 300 mg of the coxib.

8. The composition according to claim 1, wherein the coxib and the unfractionated sodium pentosan polysulfate are present in the composition in a ratio of from about 1:1 to about 1:2 by weight of the coxib to the unfractionated sodium pentosan polysulfate.

9. The composition according to claim 1 being a solid composition.

10. The composition according to claim 1, wherein the composition is a pharmaceutical composition for administration to a human.

11. A pharmaceutical or veterinary composition for oral administration comprising a therapeutically effective amount of at least one coxib and a therapeutically effective amount of unfractionated sodium pentosan polysulfate having a weight average molecular weight of about 4000 to 7000 Da contained in a hydroxy propyl methylcellulose capsule, with the proviso that the composition does not include a penetration enhancer for increasing bioavailability of the unfractionated sodium pentosan polysulfate.

12. The composition according to claim 11, wherein the unfractionated sodium pentosan polysulfate has a sulfur content in a range of from 16% to 17% by weight.

13. A method for the treatment of pain and/or inflammation in a mammal, comprising administering to the mammal an effective amount of at least one coxib in combination with an effective amount of unfractionated sodium pentosan polysulfate contained in a hydroxy propyl methylcellulose capsule, wherein the coxib and the unfractionated sodium pentosan polysulfate are administered to the mammal in the absence of administration of a penetration enhancer for increasing bioavailability of the unfractionated sodium pentosan polysulfate to the mammal.

14. The method according to claim 13, wherein the pain and/or inflammation is associated with a condition selected from the group consisting of arthritis, osteoarthritis, inflammatory arthritis, rheumatoid arthritis, gout, pseudogout, and psoriatic arthritis.

15. The method according to claim 14, wherein the osteoarthritis is hand osteoarthritis.

* * * * *